(12) United States Patent
Perez

(10) Patent No.: US 7,264,627 B2
(45) Date of Patent: Sep. 4, 2007

(54) WICKING METHODS AND STRUCTURES FOR USE IN SAMPLING BODILY FLUIDS

(75) Inventor: Edward Perez, Menlo Park, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 426 days.

(21) Appl. No.: 10/230,494

(22) Filed: Aug. 29, 2002

(65) Prior Publication Data
US 2003/0060730 A1 Mar. 27, 2003

Related U.S. Application Data

(60) Provisional application No. 60/315,873, filed on Aug. 29, 2001.

(51) Int. Cl.
*A61B 5/00* (2006.01)
(52) U.S. Cl. .................................... 606/181; 600/583
(58) Field of Classification Search ............... 606/181, 606/182, 185
See application file for complete search history.

(56) References Cited

U.S. PATENT DOCUMENTS

| 2,714,890 | A | 8/1955 | Vang |
|---|---|---|---|
| 3,086,288 | A | 4/1963 | Balamuth et al. |
| 3,208,452 | A | 9/1965 | Stern |
| 3,626,929 | A | 12/1971 | Sanz et al. |
| 3,673,475 | A | 6/1972 | Britton, Jr. |
| 3,741,197 | A | 6/1973 | Sanz et al. |
| 3,832,776 | A | 9/1974 | Sawyer |
| 4,077,406 | A | 3/1978 | Sandhage et al. |
| 4,154,228 | A | 5/1979 | Feldstein et al. |
| D254,444 | S | 3/1980 | Levine |
| 4,203,446 | A | 5/1980 | Hofert et al. |
| 4,223,674 | A | 9/1980 | Fluent et al. |
| 4,230,118 | A | 10/1980 | Holman et al. |
| 4,356,826 | A | 11/1982 | Kubota |
| 4,360,016 | A | 11/1982 | Sarrine |
| 4,441,373 | A * | 4/1984 | White .................... 73/864.02 |
| 4,449,529 | A | 5/1984 | Burns et al. |
| 4,462,405 | A | 7/1984 | Erhlich |

(Continued)

FOREIGN PATENT DOCUMENTS

DE 37 08 031 11/1987

(Continued)

*Primary Examiner*—Anhtuan T. Nguyen
*Assistant Examiner*—Darwin P. Erezo
(74) *Attorney, Agent, or Firm*—Woodard, Emhardt, Moriarty McNett & Henry LLP

(57) ABSTRACT

A sampling member defines a passageway including an inlet opening for reception of a bodily fluid therein, and a wicking member having a first portion coupled with the sampling member adjacent to the inlet opening. The wicking member further includes a second portion displaced from the first portion for initially contacting the bodily fluid. In use the sampling member is placed adjacent to an incision site with the second portion of the wicking member positioned to have the bodily fluid first contact the wicking member and thereby draw the fluid from the incision site to the inlet opening. In related embodiments there is provided a sampling system and method which further includes a lancing device to create the incision and optionally expression members to urge the bodily fluid from the incision, preferably in an integrated unit.

15 Claims, 13 Drawing Sheets

U.S. PATENT DOCUMENTS

| | | |
|---|---|---|
| 4,503,856 A | 3/1985 | Cornell et al. |
| 4,517,978 A | 5/1985 | Levin et al. |
| 4,518,384 A | 5/1985 | Tarello et al. |
| 4,535,773 A | 8/1985 | Yoon |
| 4,553,541 A | 11/1985 | Burns et al. |
| 4,564,513 A | 1/1986 | Becher et al. |
| 4,580,564 A | 4/1986 | Anderson |
| 4,622,974 A | 11/1986 | Coleman et al. |
| 4,627,445 A | 12/1986 | Garcia et al. |
| 4,637,403 A | 1/1987 | Garcia et al. |
| 4,648,408 A | 3/1987 | Hutcheson et al. |
| 4,653,511 A | 3/1987 | Goch |
| 4,653,513 A | 3/1987 | Dombrowski |
| 4,654,513 A | 3/1987 | Hennessy |
| 4,658,821 A | 4/1987 | Chiodo et al. |
| 4,685,463 A | 8/1987 | Williams |
| 4,750,489 A | 6/1988 | Berkman et al. |
| 4,787,398 A | 11/1988 | Garcia et al. |
| 4,790,979 A | 12/1988 | Terminiello et al. |
| 4,794,926 A | 1/1989 | Munsch et al. |
| 4,805,623 A | 2/1989 | Jobsis |
| 4,823,806 A | 4/1989 | Bajada |
| 4,850,973 A | 7/1989 | Jordan et al. |
| 4,858,607 A | 8/1989 | Jordan et al. |
| 4,869,249 A | 9/1989 | Crossman et al. |
| 4,873,993 A | 10/1989 | Meserol et al. |
| 4,883,068 A | 11/1989 | Dechow |
| 4,920,977 A | 5/1990 | Haynes |
| 4,924,879 A | 5/1990 | O'Brien |
| 4,953,552 A | 9/1990 | DeMarzo |
| 4,976,724 A | 12/1990 | Nieto et al. |
| 4,994,068 A | 2/1991 | Hufnagle |
| 4,994,073 A | 2/1991 | Green |
| 4,995,402 A | 2/1991 | Smith et al. |
| 5,002,054 A | 3/1991 | Ash et al. |
| 5,014,718 A | 5/1991 | Mitchen |
| 5,029,583 A | 7/1991 | Meserol et al. |
| 5,035,704 A | 7/1991 | Lambert et al. |
| 5,047,044 A | 9/1991 | Smith et al. |
| 5,054,499 A | 10/1991 | Swierczek |
| 5,066,859 A | 11/1991 | Karkar et al. |
| 5,070,886 A | 12/1991 | Mitchen et al. |
| 5,097,810 A | 3/1992 | Fishman et al. |
| 5,145,565 A | 9/1992 | Kater et al. |
| 5,152,775 A | 10/1992 | Ruppert |
| 5,163,442 A | 11/1992 | Ono |
| 5,188,118 A | 2/1993 | Terwilliger |
| 5,189,751 A | 3/1993 | Giuliani et al. |
| 5,201,324 A | 4/1993 | Swierczek |
| 5,217,480 A | 6/1993 | Haber et al. |
| 5,222,504 A | 6/1993 | Solomon |
| 5,231,993 A | 8/1993 | Haber et al. |
| 5,277,198 A | 1/1994 | Kanner et al. |
| 5,279,294 A | 1/1994 | Anderson et al. |
| 5,318,583 A | 6/1994 | Rabenau et al. |
| 5,318,584 A | 6/1994 | Lange et al. |
| 5,320,607 A | 6/1994 | Ishibashi |
| 5,320,808 A | 6/1994 | Holen et al. |
| 5,324,302 A | 6/1994 | Crouse |
| 5,353,806 A | 10/1994 | Heinzelman et al. |
| 5,368,047 A | 11/1994 | Suzuki et al. |
| 5,395,387 A | 3/1995 | Burns |
| 5,402,798 A | 4/1995 | Swierczek et al. |
| 5,415,169 A | 5/1995 | Siczek et al. |
| 5,421,816 A | 6/1995 | Lipkovker |
| 5,445,611 A | 8/1995 | Eppstein et al. |
| 5,458,140 A | 10/1995 | Eppstein et al. |
| 5,472,427 A | 12/1995 | Rammler |
| 5,474,084 A | 12/1995 | Cunniff |
| 5,487,748 A | 1/1996 | Marshall et al. |
| 5,514,152 A | 5/1996 | Smith |
| 5,529,074 A | 6/1996 | Greenfield |
| 5,554,166 A | 9/1996 | Lange et al. |
| 5,569,212 A | 10/1996 | Brown |
| 5,575,403 A | 11/1996 | Charlton et al. |
| 5,582,184 A | 12/1996 | Erickson et al. |
| 5,624,458 A | 4/1997 | Lipscher |
| 5,628,309 A | 5/1997 | Brown |
| 5,628,764 A | 5/1997 | Schraga |
| 5,630,986 A | 5/1997 | Charlton et al. |
| 5,632,410 A | 5/1997 | Moulton et al. |
| 5,680,872 A | 10/1997 | Sesekura et al. |
| 5,682,233 A | 10/1997 | Brinda |
| 5,700,695 A | 12/1997 | Yassinzadeh et al. |
| 5,707,384 A | 1/1998 | Kim |
| 5,709,699 A | 1/1998 | Warner |
| 5,714,390 A | 2/1998 | Hallowitz et al. |
| 5,720,924 A | 2/1998 | Eikmeier et al. |
| 5,730,753 A | 3/1998 | Morita |
| 5,738,244 A | 4/1998 | Charlton et al. |
| 5,746,217 A | 5/1998 | Erickson et al. |
| 5,758,643 A | 6/1998 | Wong et al. |
| 5,776,157 A | 7/1998 | Thorne et al. |
| 5,788,651 A | 8/1998 | Weilandt |
| 5,800,781 A | 9/1998 | Gavin et al. |
| 5,801,057 A | 9/1998 | Smart et al. |
| 5,810,199 A | 9/1998 | Charlton et al. |
| 5,820,570 A | 10/1998 | Erickson et al. |
| 5,823,973 A | 10/1998 | Racchini et al. |
| 5,830,219 A | 11/1998 | Bird et al. |
| 5,846,490 A | 12/1998 | Yokota et al. |
| 5,854,074 A | 12/1998 | Charlton et al. |
| 5,855,801 A | 1/1999 | Lin et al. |
| 5,863,800 A | 1/1999 | Eikmeier et al. |
| 5,871,494 A | 2/1999 | Simons et al. |
| 5,879,311 A | 3/1999 | Duchon et al. |
| 5,880,829 A | 3/1999 | Kauhaniemi et al. |
| 5,885,211 A | 3/1999 | Eppstein et al. |
| 5,891,053 A | 4/1999 | Sesekura |
| 5,916,229 A | 6/1999 | Evans |
| 5,935,075 A | 8/1999 | Casscells et al. |
| 5,938,679 A | 8/1999 | Freeman et al. |
| 5,951,492 A | 9/1999 | Douglas et al. |
| 5,951,493 A | 9/1999 | Douglas et al. |
| 5,951,582 A | 9/1999 | Thorne et al. |
| 5,964,718 A | 10/1999 | Duchon et al. |
| 5,968,063 A | 10/1999 | Chu et al. |
| 5,971,941 A | 10/1999 | Simons et al. |
| 5,997,561 A | 12/1999 | Bocker et al. |
| 6,027,459 A | 2/2000 | Shain et al. |
| 6,036,924 A | 3/2000 | Simons et al. |
| 6,048,352 A | 4/2000 | Douglas et al. |
| 6,066,103 A | 5/2000 | Duchon et al. |
| 6,071,249 A | 6/2000 | Cunningham et al. |
| 6,071,250 A | 6/2000 | Douglas et al. |
| 6,071,294 A | 6/2000 | Simons et al. |
| 6,080,116 A | 6/2000 | Erickson et al. |
| 6,093,156 A | 7/2000 | Cunningham et al. |
| 6,099,484 A | 8/2000 | Radwanski et al. |
| 6,117,630 A | 9/2000 | Reber et al. |
| 6,120,462 A | 9/2000 | Hibner et al. |
| 6,132,449 A | 10/2000 | Lum et al. |
| 6,136,013 A | 10/2000 | Marshall et al. |
| 6,139,562 A | 10/2000 | Mauze et al. |
| 6,143,164 A | 11/2000 | Heller et al. |
| 6,152,889 A | 11/2000 | Sopp et al. |
| 6,152,942 A | 11/2000 | Brenneman et al. |
| 6,155,992 A | 12/2000 | Henning et al. |
| 6,156,051 A | 12/2000 | Schraga |
| 6,159,424 A | 12/2000 | Kauhaniemi et al. |
| 6,171,325 B1 | 1/2001 | Mauze et al. |
| 6,176,865 B1 | 1/2001 | Mauze et al. |
| 6,183,489 B1 | 2/2001 | Douglas et al. |
| 6,193,673 B1 | 2/2001 | Viola et al. |

| | | | | | | |
|---|---|---|---|---|---|---|
| 6,203,504 B1 | 3/2001 | Latterell et al. | | 6,503,210 B1 | 1/2003 | Hirao et al. |
| 6,210,420 B1 | 4/2001 | Mauze et al. | | 6,506,575 B1 | 1/2003 | Knappe et al. |
| 6,210,421 B1 | 4/2001 | Bocker et al. | | 6,571,651 B1 | 6/2003 | Hodges |
| 6,228,100 B1 | 5/2001 | Schraga | | 2001/0031931 A1 | 10/2001 | Cunningham et al. |
| 6,231,531 B1 | 5/2001 | Lum et al. | | 2002/0002344 A1 | 1/2002 | Douglas et al. |
| 6,261,241 B1 | 7/2001 | Burbank et al. | | 2002/0004196 A1 | 1/2002 | Whitson |
| 6,261,245 B1 | 7/2001 | Kawai et al. | | 2002/0052618 A1 | 5/2002 | Haar et al. |
| 6,283,926 B1 | 9/2001 | Cunningham et al. | | 2002/0082543 A1 | 6/2002 | Park et al. |
| 6,285,454 B1 | 9/2001 | Douglas et al. | | 2002/0103499 A1 | 8/2002 | Perez et al. |
| 6,293,925 B1 * | 9/2001 | Safabash et al. ............ 604/136 | | 2002/0177788 A1 | 11/2002 | Hodges et al. |
| 6,306,104 B1 | 10/2001 | Cunningham et al. | | | | |
| 6,306,152 B1 | 10/2001 | Verdonk et al. | | | | |

FOREIGN PATENT DOCUMENTS

| | | |
|---|---|---|
| EP | 0 453 283 | 10/1991 |
| EP | 0 688 532 A2 | 12/1995 |
| JP | 04194660 A1 | 11/1990 |
| JP | 2000116768 A2 | 4/2000 |
| WO | WO85/04089 | 9/1985 |
| WO | WO95/10223 | 4/1995 |
| WO | WO97/42882 | 11/1997 |
| WO | WO97/42888 | 11/1997 |
| WO | WO97/43962 | 11/1997 |
| WO | WO00/40150 | 7/2000 |
| WO | WO 01/00090 A1 | 1/2001 |
| WO | WO 01/24931 | 4/2001 |
| WO | WO 01/34029 A1 | 5/2001 |
| WO | WO 01/64105 | 9/2001 |
| WO | WO 01/66010 A1 | 9/2001 |
| WO | WO 01/73395 A2 | 10/2001 |
| WO | WO 02/056769 A1 | 7/2002 |

| | | |
|---|---|---|
| 6,315,738 B1 | 11/2001 | Nishikawa et al. |
| 6,319,210 B1 | 11/2001 | Douglas et al. |
| 6,332,871 B1 | 12/2001 | Douglas et al. |
| 6,352,514 B1 | 3/2002 | Douglas et al. |
| 6,364,889 B1 | 4/2002 | Kheiri et al. |
| 6,364,890 B1 | 4/2002 | Lum et al. |
| 6,375,627 B1 | 4/2002 | Mauze et al. |
| 6,379,317 B1 | 4/2002 | Kintzig et al. |
| 6,379,969 B1 | 4/2002 | Mauze et al. |
| 6,391,005 B1 | 5/2002 | Lum et al. |
| 6,402,701 B1 | 6/2002 | Kaplan et al. |
| 6,402,704 B1 | 6/2002 | McMorrow |
| 6,409,740 B1 | 6/2002 | Kuhr et al. |
| 6,461,496 B1 | 10/2002 | Feldman et al. |
| 6,472,220 B1 | 10/2002 | Simons et al. |
| 6,485,439 B1 | 11/2002 | Roe et al. |
| 6,488,891 B2 | 12/2002 | Mason et al. |
| 6,491,709 B2 | 12/2002 | Sharma et al. |
| 6,497,845 B1 | 12/2002 | Sacherer |

* cited by examiner

WICKING METHODS AND STRUCTURES FOR USE IN SAMPLING BODILY FLUIDS

REFERENCE TO RELATED APPLICATIONS/PATENTS

This application is related to and claims priority from provisional U.S. Patent Applications, Ser. No. 60/315,873 filed on Aug. 29, 2001 (1107P). The disclosure in the foregoing application is hereby incorporated by reference.

BACKGROUND OF THE INVENTION

1. Field of the Invention

The present invention relates to the sampling of a bodily fluid obtained from an incision in the skin, and more particularly to devices and methods for drawing the fluid to the inlet opening of a sampling device. The invention also includes the combination of such devices and methods with incising, expressing, and/or testing systems.

2. Description of the Prior Art

General Fluid Testing

The acquisition and testing of bodily fluids is useful for many purposes, and continues to grow in importance for use in medical diagnosis and treatment, and in other diverse applications. In the medical field, it is desirable for lay operators to perform tests routinely, quickly and reproducibly outside of a laboratory setting, with rapid results and a readout of the resulting test information. Testing can be performed on various bodily fluids, and for certain applications is particularly related to the testing of blood and/or interstitial fluid. Such fluids can be tested for a variety of characteristics of the fluid, or analytes contained in the fluid, in order to identify a medical condition, determine therapeutic responses, assess the progress of treatment, and the like.

General Test Steps

The testing of bodily fluids basically involves the steps of obtaining the fluid sample, transferring the sample to a test device, conducting a test on the fluid sample, and displaying the results. These steps are generally performed by a plurality of separate instruments or devices.

Acquiring—Vascular

One method of acquiring the fluid sample involves inserting a hollow needle or syringe into a vein or artery in order to withdraw a blood sample. However, such direct vascular blood sampling can have several limitations, including pain, infection, and hematoma and other bleeding complications. In addition, direct vascular blood sampling is not suitable for repeating on a routine basis, can be extremely difficult and is not advised for patients to perform on themselves.

Acquiring—Incising

The other common technique for collecting a bodily fluid sample is to form an incision in the skin to bring the fluid to the skin surface. A lancet, knife or other cutting instrument is used to form the incision in the skin. The resulting blood or interstitial fluid specimen is then collected in a small tube or other container, or is placed directly in contact with a test strip. The fingertip is frequently used as the fluid source because it is highly vascularized and therefore produces a good quantity of blood. However, the fingertip also has a large concentration of nerve endings, and lancing the fingertip can therefore be painful. Alternate sampling sites, such as the palm of the hand, forearm, earlobe and the like, may be useful for sampling, and are less painful. However, they also produce lesser amounts of blood. These alternate sites therefore are generally appropriate for use only for test systems requiring relatively small amounts of fluid, or if steps are taken to facilitate the expression of the bodily fluid from the incision site.

Various methods and systems for incising the skin are known in the art. Exemplary lancing devices are shown, for example, in U.S. Pat. No. Re 35,803, issued to Lange, et al. on May 19, 1998.; U.S. Pat. No. 4,924,879, issued to O'Brien on May 15, 1990; U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 6,332,871, issued to Douglas et al. on Dec. 25, 2001; and U.S. Pat. No. 5,964,718, issued to Duchon et al. on Oct. 12, 1999. A representative commercial lancing device is the Accu-Chek Softclix lancet.

Expressing

Patients are frequently advised to urge fluid to the incision site, such as by applying pressure to the area surrounding the incision to milk or pump the fluid from the incision. Mechanical devices are also known to facilitate the expression of bodily fluid from an incision. Such devices are shown, for example, in U.S. Pat. No. 5,879,311, issued to Duchon et al. on Feb. 16, 1999; U.S. Pat. No. 5,857,983, issued to Douglas on Jan. 12, 1999; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 5,964,718, issued to Duchon et al. on Oct. 12, 1999; and U.S. Pat. No. 6,086,545, issued to Roe et al. on Jul. 11, 2000. A representative commercial product that promotes the expression of bodily fluid from an incision is the Amira AtLast blood glucose system.

Sampling

The acquisition of the produced bodily fluid, hereafter referred to as the "sampling" of the fluid, can take various forms. Once the fluid specimen comes to the skin surface at the incision, a sampling device is placed into contact with the fluid. Such devices may include, for example, systems in which a tube or test strip is either located adjacent the incision site prior to forming the incision, or is moved to the incision site shortly after the incision has been formed. A sampling tube may acquire the fluid by suction or by capillary action. Such sampling systems may include, for example, the systems shown in U.S. Pat. No. 6,048,352, issued to Douglas et al. on Apr. 11, 2000; U.S. Pat. No. 6,099,484, issued to Douglas et al. on Aug. 8, 2000; and U.S. Pat. No. 6,332,871, issued to Douglas et al. on Dec. 25, 2001. Examples of commercial sampling devices include the Roche Compact, Amira AtLast, Glucometer Elite and Therasense FreeStyle test strips.

Testing General

The bodily fluid sample may be analyzed for a variety of properties or components, as is well known in the art. For example, such analysis may be directed to hematocrit, blood glucose, coagulation, lead, iron, etc. Testing systems include such means as optical (e.g., reflectance, absorption, fluorescence, Raman, etc.), electrochemical, and magnetic means for analyzing the sampled fluid. Examples of such test systems include those in U.S. Pat. No. 5,824,491, issued to Priest et al. on Oct. 20, 1998; U.S. Pat. No. 5,962,215, issued to Douglas et al. on Oct. 5, 1999; and U.S. Pat. No. 5,776,719, issued to Douglas et al. on Jul. 7, 1998.

Typically, a test system takes advantage of a reaction between the bodily fluid to be tested and a reagent present in the test system. For example, an optical test strip will generally rely upon a color change, i.e., a change in the wavelength absorbed or reflected by dye formed by the reagent system used. See, e.g., U.S. Pat. Nos. 3,802,842; 4,061,468; and 4,490,465.

Blood Glucose

A common medical test is the measurement of blood glucose level. The glucose level can be determined directly by analysis of the blood, or indirectly by analysis of other fluids such as interstitial fluid. Diabetics are generally instructed to measure their blood glucose level several times a day, depending on the nature and severity of their diabetes. Based upon the observed pattern in the measured glucose levels, the patient and physician determine the appropriate level of insulin to be administered, also taking into account such issues as diet, exercise and other factors.

In testing for the presence of an analyte such as glucose in a bodily fluid, test systems are commonly used which take advantage of an oxidation/reduction reaction which occurs using an oxidase/peroxidase detection chemistry. The test reagent is exposed to a sample of the bodily fluid for a suitable period of time, and there is a color change if the analyte (glucose) is present. Typically, the intensity of this change is proportional to the concentration of analyte in the sample. The color of the reagent is then compared to a known standard which enables one to determine the amount of analyte present in the sample. This determination can be made, for example, by a visual check or by an instrument, such as a reflectance spectrophotometer at a selected wavelength, or a blood glucose meter. Electrochemical and other systems are also well known for testing bodily fluids for properties on constituents.

Invention's Advantages

The present invention provides for enhancing the sampling of a bodily fluid received from an incision, particularly by drawing the fluid to the inlet opening of the sampling device. A wicking member is positioned to have one end contact the fluid appearing at the incision and an opposed end located adjacent to the inlet opening. The fluid is thereby drawn from the incision to the inlet opening, thereby enhancing the potential for the fluid to be successfully acquired by the sampling device.

SUMMARY OF THE INVENTION

The present invention provides various systems and methods for the sampling of bodily fluid from an incision in the skin. The sampling is achieved using a wicking member that extends from a first location adjacent to the inlet opening of the sampling passageway to a second location adjacent to the incision site. The invention encompasses separate sampling devices as well as combination systems including incising, expression and/or testing systems.

In accordance with one aspect of the present invention, there is provided a wicking member that is attached at one end to a test strip or other sampling device. The wicking member is attached at a location adjacent to the inlet opening of the sampling device such that fluid moving along the wicking member will contact and be drawn into the inlet opening. The wicking member extends outwardly from the sampling device in the direction of the incision site, and includes an end located adjacent to the incision site. The wicking member may be positioned at the incision site prior or subsequent to the formation of the incision.

In another aspect, the present invention includes the use of a wicking member that is positioned adjacent to, but not directly connected to, the sampling device. In one embodiment, the incision device extends adjacent to the inlet opening and bodily fluid wicking up the incision device contacts and is drawn into the inlet opening.

The present invention further encompasses the combination of the foregoing systems with each other, and with incising, expressing and/or testing systems and methods, particularly in a single, integrated device.

DESCRIPTION OF THE PREFERRED EMBODIMENT

Figure 1:
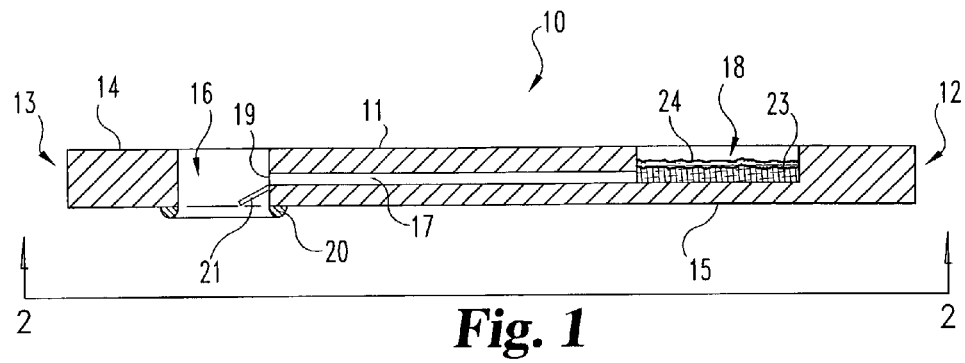
FIG. 1 is a side, cross-sectional view of a test strip in accordance with the present invention.
Figure 2:
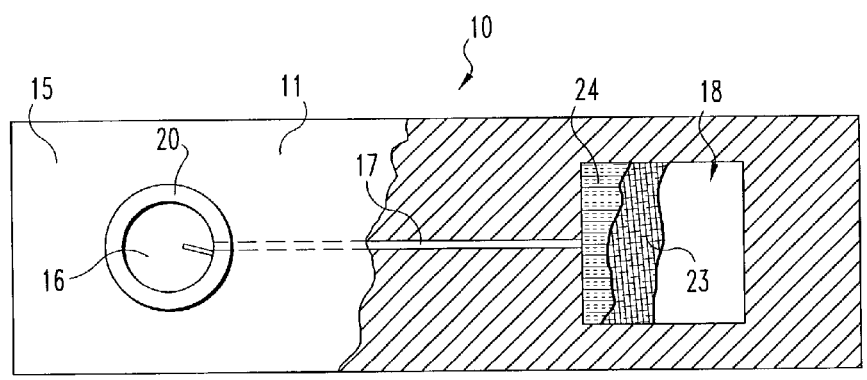
FIG. 2 is a bottom, plan view of the test strip of FIG. 1, partially in cross section.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices and methods, and such further applications of the principles of the invention as illustrated therein being contemplated as would normally occur to one skilled in the art to which the invention relates.

Wicking Member—General

The present invention provides a variety of devices and methods which separately or in combination are useful in enhancing the sampling of fluid from an incision in the skin. The invention is useful to draw the bodily fluid from the incision site to the sampling passageway of a sampling device. As used herein, the term sampling passageway encompasses any structure for receiving and transporting the bodily fluid, including but not limited to a passageway formed in a test strip, conduit, or other structure, and particularly includes passageways which receive and transport the bodily fluid by capillary action or by vacuum. The term sampling device includes any device for acquiring a sample of the bodily fluid, which may also include means for testing the bodily fluid. The sampling of the fluid utilizes structures to draw the bodily fluid to the inlet opening of the sampling device. The invention particularly relates to the use of a wicking member, incising device, or other element to draw the bodily fluid to the inlet opening of the sampling passageway.

The fluid is obtained from an incision formed in the surface of the skin. The incising of the skin may be accomplished by any suitable means, including cutting with a mechanical instrument, laser, high speed fluid stream, etc. Of these, lancing the skin is most common and is preferred, and specific descriptions herein use lancing for purposes of example. It will be appreciated, however, that lancing is only exemplary, and all forms of making an incision in the skin are included. As used herein, the term "incision" is intended to cover any opening in the skin that permits direct access to the bodily fluid. The term "incising" is intended to mean generally any way to form an incision in the skin to enable fluid to be accessed directly. The term "incision site" is intended to include the site where an incision either has been or will be formed, unless from the context or express language it is clear otherwise.

The depth of penetration generally controls the fluid produced, particularly in combination with the characteristics of the incision site. The present invention is useful with various bodily fluids, including blood or interstitial fluid. The incising device may be configured for production of either blood or interstitial fluid, for example, by controlling the distance which the incising device extends into the user's skin. For example, a depth of 0.25 mm to 4 mm will typically produce blood from the dermis, while a depth of 0.05 mm to 0.5 mm will produce interstitial fluid from the epidermis.

It will be appreciated from the following description that the present invention is useful independently of the presence or type of incising, expressing or testing systems. In certain embodiments, the present invention may comprise devices, and associated methods, which are limited only to sampling of fluid from an incision. In other embodiments, the sampling mechanisms and methods are combined with incising, expressing and/or testing systems. The present invention finds particular advantage in combination with such other systems as a part of an overall integrated device.

The present invention facilitates the movement of the bodily fluid from the incision site to the inlet opening of the passageway used for sampling the fluid. The sampling device may comprise a test strip, capillary tube, or any other structure that receives the bodily fluid. In one embodiment, the sampling device includes a passageway that receives and transports the bodily fluid by capillary action.

The invention addresses the fact that the bodily fluid will initially pool at the incision site, and it is desired that some mechanism be provided that will cause the fluid to move in the appropriate direction toward the inlet opening of the sampling passageway. It may be difficult or undesirable to place the inlet opening close enough to the incision site to directly contact the bodily fluid as it appears. The present invention avoids the need to do this by using a wicking member that extends from a first location adjacent to the inlet opening to a second location adjacent to the incision site. The bodily fluid is drawn along the wicking member from the incision site to the inlet opening and is thereafter drawn into the sampling passageway.

In one approach, the wicking member is attached directly to the sampling device. For example, in accordance with this embodiment, a test strip defines a passageway for receiving the bodily fluid. The test strip includes an exterior surface that includes an inlet opening which communicates with the sampling passageway. The wicking member is attached to or formed integrally with the exterior surface of the test strip at a position adjacent to the inlet opening. Therefore, bodily fluid moving along the wicking member will contact the test strip sufficiently close to the inlet opening that it will be drawn into the inlet opening, and therefore the sampling passageway. Similarly in an alternate embodiment, the sampling device comprises a capillary tube having an inlet opening, and a wicking member that is attached to the capillary tube adjacent to the inlet opening.

The wicking member extends from the inlet opening toward the incision site. The wicking member has a length and shape which will position a portion of the wicking member close enough to the incision site that the bodily fluid appearing at the site will contact that portion of the wicking member. The wicking member preferably is configured to have an end which is located adjacent to the incision site.

The wicking member may have any of a wide variety of configurations. The wicking member is preferably an elongated member, more preferably including a uniform cross-sectional size and shape. The size of the wicking member may vary substantially with the particular application.

The wicking member may also be designed to be normally extended from the sampling device, or to be deployed in some fashion at the desired time. For example, in one embodiment the wicking member comprises an elongated member attached or formed integrally with the sampling device and permanently extending in the desired manner from the sampling device. In an alternate embodiment, the wicking member is folded against the sampling device or otherwise retracted from its extended position until deployed. The wicking member may be deployed in various ways, such as by release of a retaining film or other member, by affirmatively moving the wicking member to the extended position, or by other means. In one approach, the operation of an incising device, e.g. a lancet, to form the incision in the skin also triggers the release of the wicking member, such as by moving a retaining film that otherwise holds the wicking member in the retracted position.

In an alternative approach, the wicking member is positioned close to the inlet opening of the sampling device, but is not attached directly thereto. In one embodiment, a separate wicking member is attached to a housing or other structure to be located in position to draw the bodily fluid from the incision site to the inlet opening. In another embodiment, the incising device is used to perform this function. For example, the incising device includes, for example, a lancet that is first used to form the incision, and then is withdrawn from the incision but retained at a position with the tip of the lancet sufficiently close to the incision site to contact the bodily fluid as it collects. The body of the lancet extends closely adjacent to the inlet opening of the sampling passageway. Therefore, when the bodily fluid wicks along the lancet it contacts the inlet opening and is drawn into the passageway.

In each of the various embodiments, the bodily fluid is drawn along the wicking member from the incision site to the inlet opening. This action is enhanced by using a wicking member that is formed of a material that is naturally hydrophilic or has been treated to be hydrophilic, or which is covered, e.g., coated, with a hydrophilic material. Such variety of ways for providing a hydrophilic surface for the wicking member are well known in the art, and are encompassed by the present invention.

Referring to the drawings, a first preferred embodiment of the test strip system of the present invention is shown in FIGS. 1-4. The strip 10 is preferably combined in an integrated unit which further includes components for the purposes of incising the skin and testing the produced fluid sample. The test strip 10 includes a body 11 having first end 12, second end 13, top surface 14, and bottom surface 15. The body further includes an aperture 16 extending from the top surface to the bottom surface, a sampling passageway 17, and a test area 18. The sampling passageway 17 includes an inlet opening 19 which communicates with the aperture 16 at a location spaced from the bottom surface 15.

A sealing member 20 is attached to or formed integrally with the bottom surface 15 of the body 11 in a position surrounding the aperture 16. The sealing member is constructed from a biocompatible material such as silicon, urethane, rubber, latex and various other natural and synthetic materials. In one embodiment, the sealing member is configured and formed of a material to be deformable when pressed against the skin, helping to assure a fluid tight seal with the skin. Alternatively, the sealing member may be formed from a rigid material, such as a plastic, metal, ceramic or other material to provide a seal when pressed against the user's skin. In most instances a rigid material is equally useful because of the pliability of the skin. However, a deformable sealing member may be preferable in certain instances to further ensure that a fluid-tight seal forms with the skin.

In a further aspect, the sealing member preferably includes a hydrophobic surface. The seal with the skin will resist passage of the bodily fluid under the sealing member, but the use of a hydrophobic surface enhances the function of the sealing member. The surface of the sealing member may be provided to be hydrophobic in various known ways, all of which are intended to be encompassed by the present invention. For example, the sealing member may be formed from a hydrophobic material, or may be provided with a hydrophobic coating. In addition, certain hydrophilic materials can be treated to be made hydrophobic in accordance with known techniques.

The test strip further includes a wicking member 21 attached to the strip adjacent to the inlet opening 19. The wicking member is shown attached slightly below the inlet opening, although the member may also be attached at a location level with or above the inlet opening. The attachment location is selected to provide that the bodily fluid traveling along the wicking member 21 will contact the inlet opening and thereby be drawn into the passageway 17. It will be appreciated that the functioning of the wicking member 21 may be enhanced by providing for the surface defining the opening 16 to be hydrophilic in the area adjacent to the inlet opening, and further by providing for the more distant portions of the surface to be hydrophobic. Therefore, any fluid contacting the surface will preferentially be drawn toward the inlet opening, rather than away from it.

Figure 3:
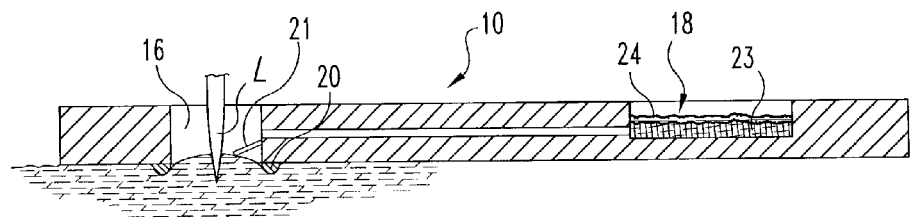
FIG. 3 is a side, cross-sectional view of the test strip of FIG. 1, showing the test strip positioned adjacent to the skin.

The wicking member 21 extends outwardly from the surface of the test strip toward the center of the opening 16. More particularly, the wicking member extends to preferably position its distal end adjacent to the location of the incision site. As shown in FIG. 3, for example, the wicking member 21 has its end position adjacent to the location at which the lancet L forms the incision in the skin. In this manner, the end of the wicking member 21 is located such that it will contact the bodily fluid collecting at the incision site.

The use of the test strip system 10 proceeds as follows. The test strip 10 is positioned against the skin such that the skin bears against the sealing member 20, forming a fluid tight seal therewith. This assures that any fluid exiting the incision will be retained within the opening 16, rather than moving out under the test strip body. The sealing member further provides an expression force pulling on the skin to open the incision when formed. Also, the contact of the skin with the sealing member locates the skin at a controlled position to facilitate the formation of the incision at a desired depth and position. Because the sealing member projects outwardly from the bottom surface, the location of the skin within the opening is lowered, which in some embodiments is useful to position the skin at a desired location relative to the inlet opening 19 of the sampling passageway.

The lancing device L is extended downwardly through opening 16 to lance the skin to the desired, controlled depth. The lancet is then withdrawn (FIG. 4) and bodily fluid 22 is allowed to form at the incision site. As the fluid accumulates to a sufficient extent, it contacts the free end of the wicking member 21 and is drawn along the hydrophilic surface of the member to the entrance 19 of the passageway 17, from which the fluid is drawn into and through the passageway, such as by capillary action. The fluid moves to the test area 18, such as by wicking into an absorbent material 23, and there contacts the test reagent 24 positioned on top of the wicking material.

Figure 4:
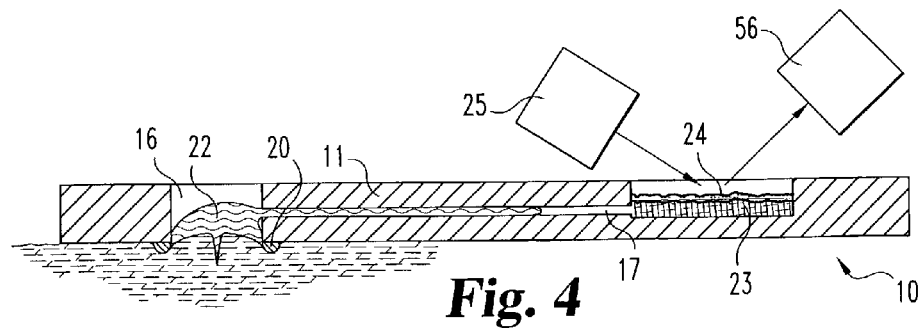
FIG. 4 is a side, cross-sectional view of the test strip of FIG. 1, showing the bodily fluid being acquired by the capillary passageway in the test strip.
Figure 5:
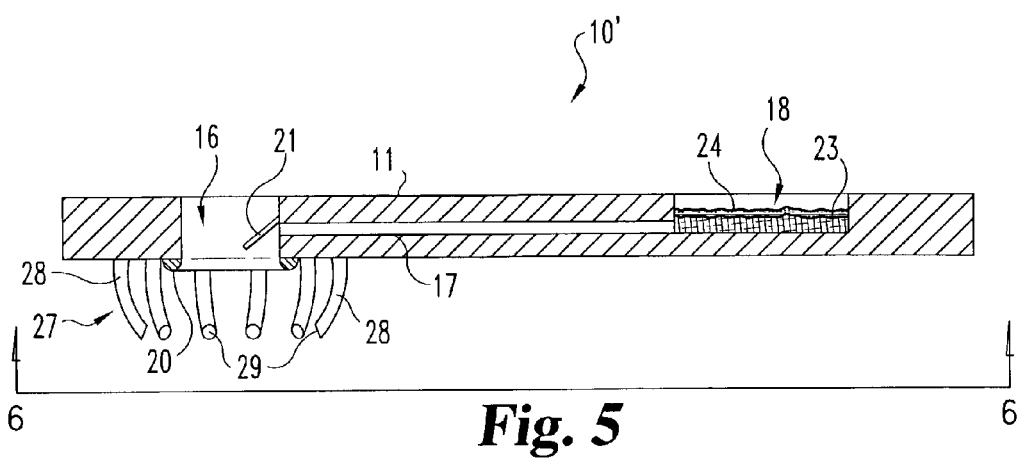
FIG. 5 is a side, elevational view of an integrated fluid testing device according to a second embodiment of the present invention which includes a fluid expression system.

The fluid is thereby presented in the test area and can be tested by conventional means, such as by reacting the fluid with the test reagent and analyzing the reaction product by optical or electrochemical means. For example, shown diagrammatically in FIG. 4 is a light source 25 for directing light against the test reagent, and a blood glucose meter 26 for receiving light reflected from the test reagent. In conventional fashion, the meter analyzes the reflected light to determine the result of the reaction between the bodily fluid and the test reagent. In this same manner, a wide variety of analytes and properties of the fluid may be determined. Useful optical, electrochemical and other test systems are well known in the art and therefore are not further described herein.

In an alternative embodiment, the test strip includes a constriction system utilizing several discrete members which engage the skin and pinch it inwardly to aid in expressing the bodily fluid from the incision. Referring in particular to FIGS. 5-8, there is shown an embodiment of the test strip 10' including a constricting system 27 attached to the underside thereof. The constricting system includes several discrete, deformable elements 28, each element defining a surface 29 to engage the skin and move it inwardly to constrict the skin.

Figure 6:
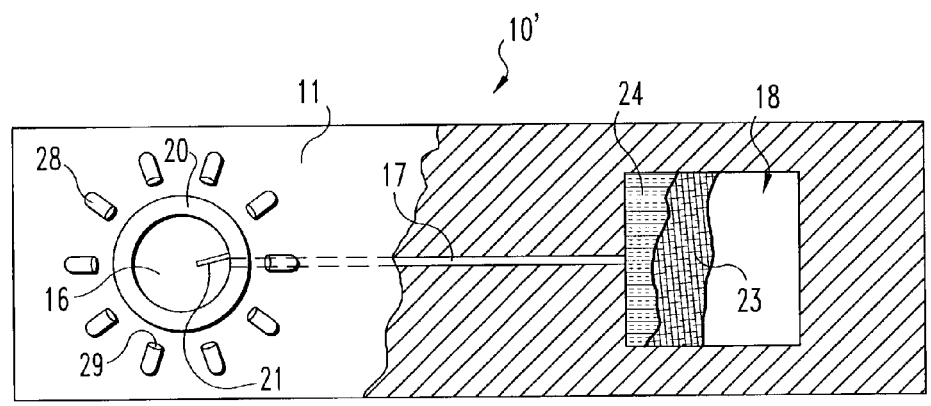
FIG. 6 is a bottom, plan view of the test strip of FIG. 5, partially in cross section.
Figure 7:
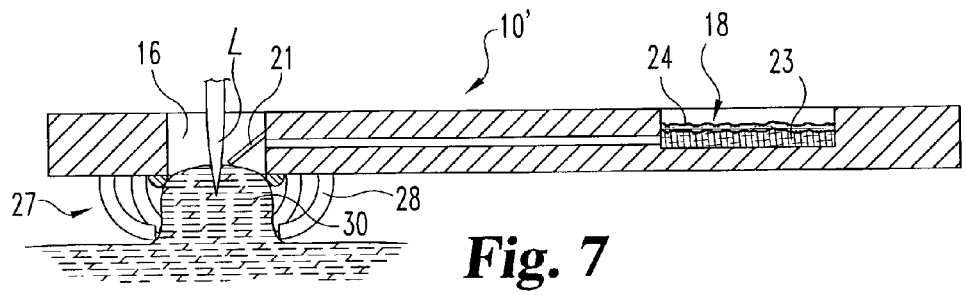
FIGS. 7-8 are partial, cross-sectional views of the fluid testing device of FIG. 5, showing in particular the acquisition of the fluid by the capillary passageway.
Figure 8:
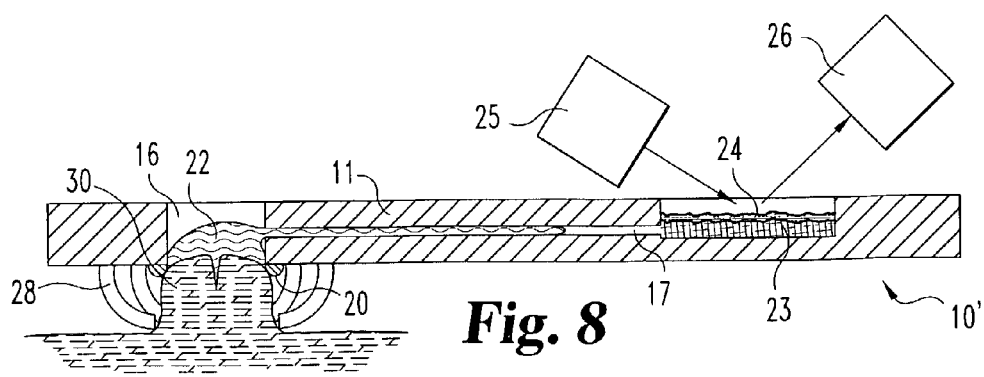

The constricting elements are selected to be spaced apart and to generally surround the incision site. The elements are therefore preferably provided such that at least two elements are positioned to be on opposite sides of the incision site, but also any additional number of elements may be included. In a preferred embodiment, the elements include skin-engaging surfaces 29 positioned to fall within a circular pattern (FIG. 6). The elements preferably deform in a manner to move the skin-engaging surfaces in a radially-inward direction.

The strip 10' otherwise is constructed substantially as shown in FIGS. 1-4, and is used as follows. The test strip 10' is pressed against the skin such that the arms 28 engage the skin and deform inwardly, thereby creating and retaining a bulged skin area 30. The skin is drawn upward and inward to an extent that it bears against the sealing member 16, forming a fluid tight seal therewith. This assures that any fluid exiting the incision will be retained within the opening 16, rather than moving out under the test strip body. The sealing ring further functions pull on the skin to open the incision when formed.

The lancing device L is extended downwardly through opening 16 to lance the skin to the desired, controlled depth. The lancet is then withdrawn (FIG. 8) and bodily fluid 22 is allowed to form at the incision site. When the fluid accumulates to a sufficient extent, it contacts the member 21 and moves to the entrance of the passageway 17, and is thereafter drawn into and through the passageway to the test area 18.

Recessed Underside

In another aspect of the present invention, there is provided a test strip including a surface between the inlet opening and the bottom surface that is recessed away from the incision site. By recessing the bottom surface, the bodily fluid contacts the inlet opening before it contacts and is drawn along the bottom surface.

Referring to the drawings, there is shown a test strip 50 (FIG. 9) in accordance with another preferred embodiment of the present invention. Test strip 50 includes a body 51 having first end 52, second end 53, top surface 54 and bottom surface 55. The body further defines an aperture 56, a test area 57, and a sampling passageway 58 communicating with the aperture at an inlet opening 59 spaced from the bottom surface. The sampling passageway extends generally away from the aperture 56 in the direction of the first end 52. A wicking member 60 is connected with and extends from a location adjacent the inlet opening 59.

The test strip is configured to promote contact of the bodily fluid with the wicking member 60 and the inlet opening 59 prior to making contact with other portions of the test strip. An incision is made within the area encompassed by the aperture, and the desire then is to cause the bodily fluid coming from the incision to contact the inlet opening in preference to any of the surrounding portions of the test strip. In a preferred aspect of the present invention, this is accomplished by recessing at least a portion of the surface between the inlet opening and the bottom surface, and by providing the wicking member 60 to pull the fluid to the inlet opening. In another aspect, the other portions of the bottom surface, for example the portion 62 on the opposite side of the aperture, are also configured or located to inhibit contact with the bodily fluid. In one approach, the incision 61 is formed closer to the side of the aperture 56 at which the inlet opening is located. In another approach, the test strip may also include recessed portions at the other locations surrounding the incision site.

Accordingly, the test strip 50 includes a recessed surface 63 between the inlet opening 59 and the bottom surface 55. As used herein, the term "recessed surface" refers to the surface between the location of the inlet opening and the bottom surface. This surface is recessed in the direction away from the incision site, i.e., away from the aperture 56 in the direction of the first end 52. The term "recess" encompasses any configuration which displaces the closest portion of the planar, bottom surface 55 away from the aperture 56. For example, the surface could be curved inwardly or outwardly, or could have a series of steps of other contours.

Figure 9:
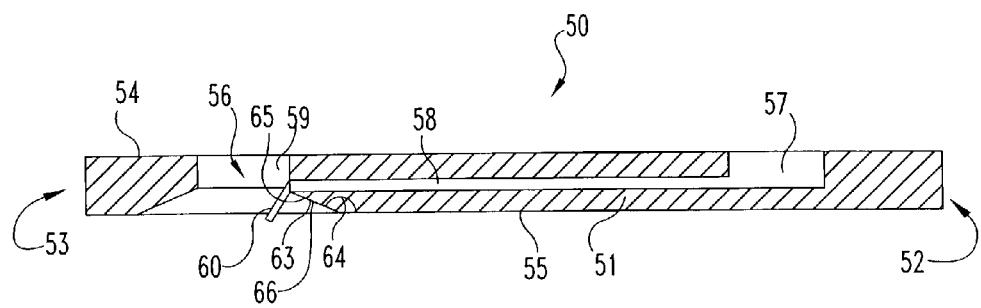
FIG. 9 is a side, cross-sectional view of an alternate embodiment of a test strip of the present invention.
Figure 10:
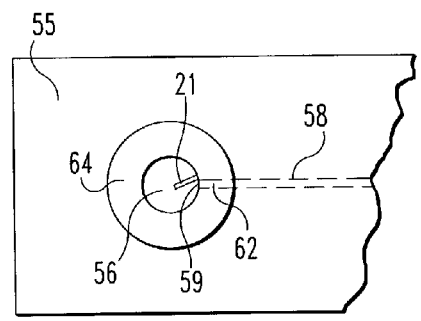
FIG. 10 is a partial, bottom plan view of the test strip of FIG. 9.

As shown in FIG. 9, in a preferred embodiment the test strip includes a surface 62 which tapers away from the inlet opening 58 to the bottom surface 55. In this configuration, the surface 63 extends at an obtuse angle 64 from the bottom surface.

The test strip 50 may also include a sealing member (not shown), as described with respect to FIGS. 1-4. Such a sealing member may be located along the recessed surface(s) and/or on the planar, bottom surface. The sealing member then complements the action of the recessed surfaces in that bodily fluid that happens to move against the sealing member will be inhibited from passing between the test strip and the skin.

The test strip may also be provided with a hydrophobic surface adjacent the aperture to further inhibit wicking away from the inlet opening. For example, the portions of the bottom surface adjacent to the aperture 56 are preferably provided with a hydrophobic surface. Further, the recessed surface 63 may be made hydrophobic to prevent wicking of the bodily fluid toward the bottom surface. In a particularly preferred embodiment, the recessed surface includes two different regions. A first region 65 adjacent the bottom surface is provided to be hydrophobic to inhibit wicking toward the bottom surface. A second region 66 adjacent the inlet opening is provided to be hydrophilic to promote wicking of the bodily fluid toward the inlet opening. Thus, fluid contacting the recessed surface will be directed away from the bottom surface and toward the inlet opening.

Figure 11:
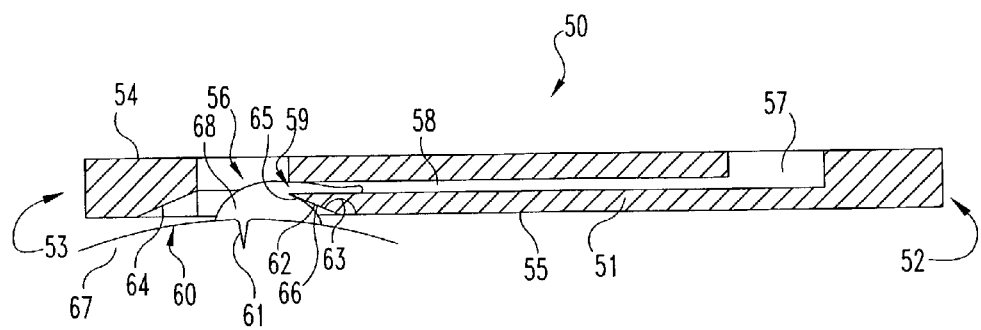
FIG. 11 is a side, cross-sectional view of the embodiment of FIG. 9, showing the acquisition of the bodily fluid.

The test strip 50 is used as follows. The test strip is positioned adjacent to the skin, either resting against the skin or spaced slightly away from the skin. If a sealing member is included, then the test strip is placed sufficiently close to the skin to have the sealing member contact and seal with the skin. An incision is formed in the skin, and a droplet of bodily fluid forms at the incision site. As the droplet grows, it eventually contacts the wicking member 60 and moves to the inlet opening 59, and is thereafter drawn into the passageway 58, such as by capillary action (FIG. 11). The bodily fluid then moves through the passageway 58 to the test area 57 for analysis.

Figure 12:
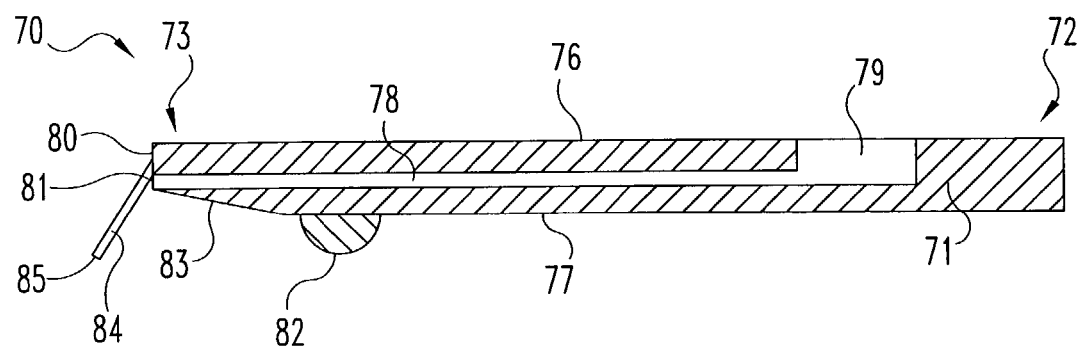
FIG. 12 is a side, cross-sectional view of another alternate embodiment of a test strip of the present invention.
Figure 13:
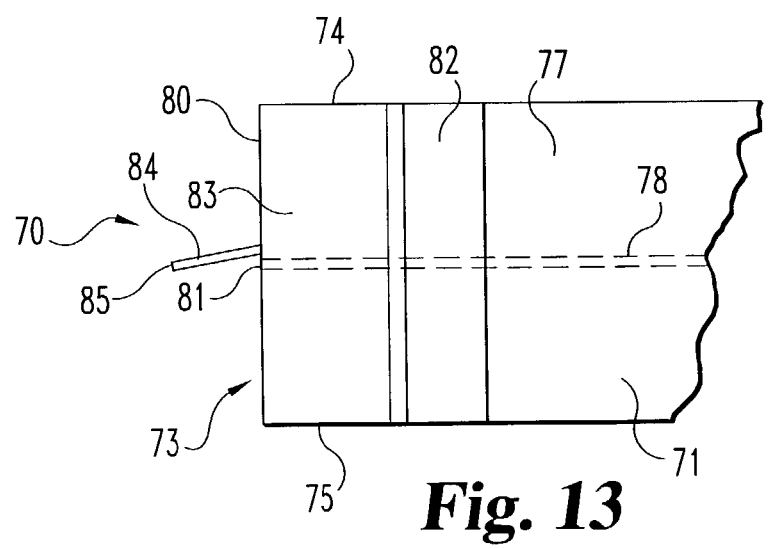
FIG. 13 is a partial, bottom plan view of the test strip of FIG. 12.
Figure 14:
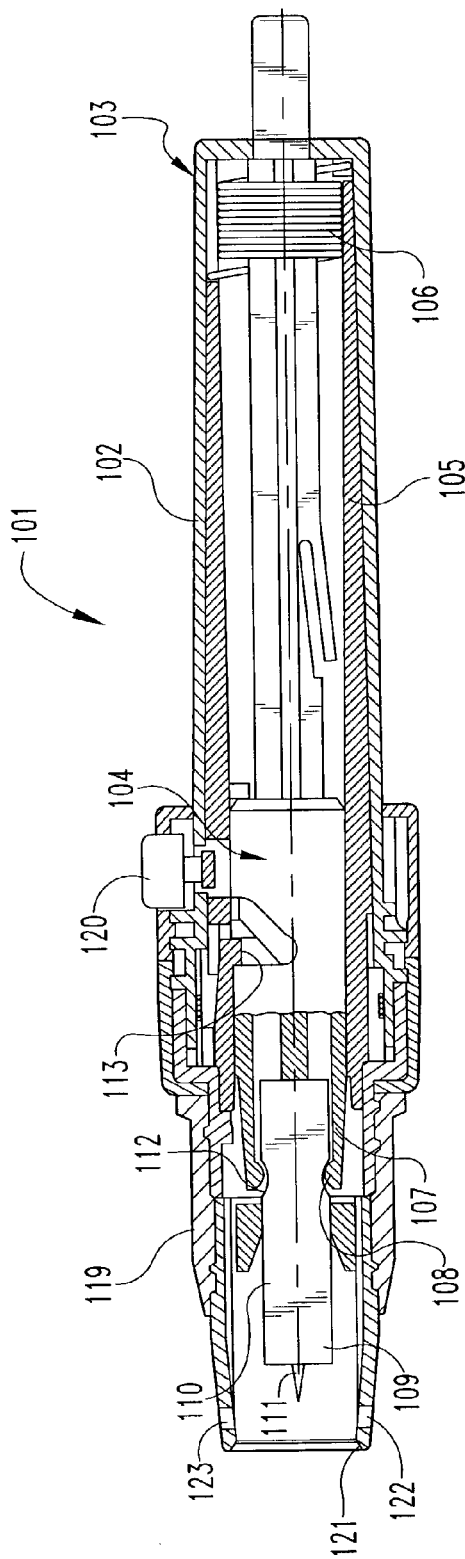
FIG. 14 is a side, cross-sectional view of a lancing device useful with a sampling system of the present invention.
Figure 15:
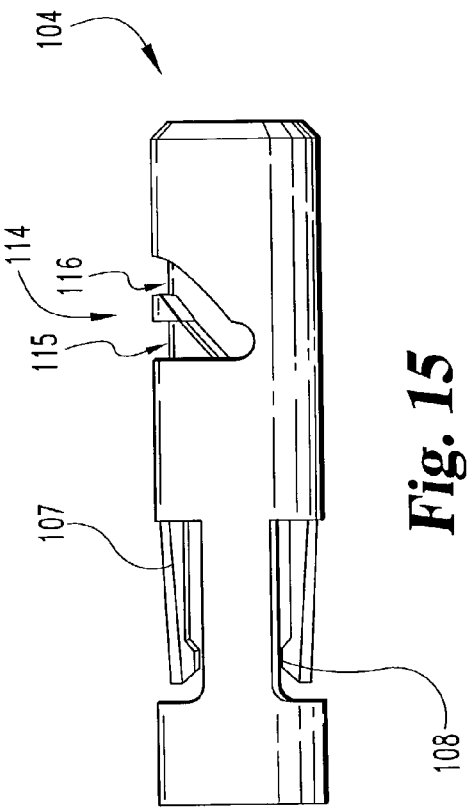
FIG. 15 is a side, elevational view of a lancet holder useful in the device of FIG. 14.
Figure 16:
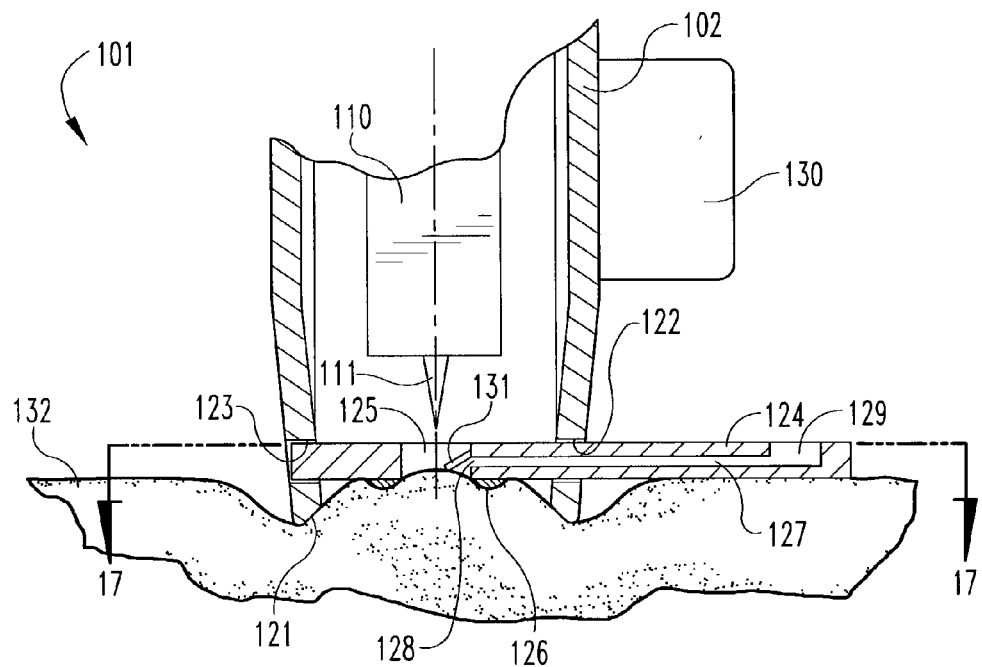
FIG. 16 is a partial, cross-sectional view of the skin-engaging portion of the device of FIG. 14, and further showing the test strip mounted therein.
Figure 17:
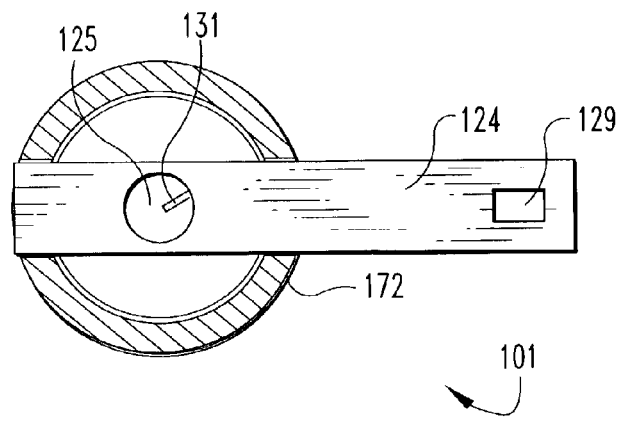
FIG. 17 is a cross-sectional view of the device of FIG. 16 taken along the line 17-17 and viewed in the direction of the arrows.

An alternate embodiment of the test strip of the present invention is shown in FIGS. 12 and 13. The test strip 70 includes a body 71 including a first end 72, second end 73, first side edge 74, second side edge 75, top surface 76 and bottom surface 77. The test strip 70 further defines a sampling passageway 78 communicating between a test region 79 and an end edge 80 located at the second end 73. The sampling passageway 78 includes an inlet opening 81 communicating with the end edge at a location displaced from the bottom surface 77.

A sealing member 82 is located on the bottom surface 77 in a position to contact and seal with the skin when the test strip is in use. The sealing member 82 is aligned under the inlet opening 81 such that bodily fluid present near the inlet opening is thereby blocked from passing under the test strip. In one embodiment, the sealing member preferably extends from the first edge 74 to the second edge 75. In an alternate embodiment (not shown), the sealing member extends less than the full width of the test strip, or is otherwise configured other than extending linearly across the test strip. For example, in one approach the sealing member forms a semi-circle contacting the end edge 80 at two locations on either side of the inlet opening. In another approach, the sealing member forms a V-shape extending inwardly of the test strip from the two corners formed between the end edge 80 and the two side edges 74 and 75.

The test strip 70 further includes additional features as described with respect to the previous embodiments. The test strip includes a recessed surface 83 connecting between the inlet opening 81 and the bottom surface 77. At least a lower portion of the recessed surface is preferably provided to be hydrophobic to preclude wicking of bodily fluid along the recessed surface toward the underside of the test strip. The sealing member 82 and the bottom surface 77 are also preferably provided to be hydrophobic to resist wicking of bodily fluid.

The test strip 70 further includes a wicking member 84 connected with the strip at a location adjacent to the inlet opening 81. In this embodiment, the wicking member is shown as being attached closely above the inlet opening, although alternate locations adjacent to the inlet opening would also be suitable. The wicking member extends downwardly from the end edge 80 (FIG. 12) to be positioned adjacent to the incision site when the test strip is in use. The wicking member 84 is also shown (FIG. 13) as extending from the end edge 80 at a slight angle, in order to locate the distal end 85 in line with the center of the test strip 70 and the inlet opening 81.

The test strip 70 is used in a similar fashion as the previous embodiments. The test strip is placed adjacent to the skin with the sealing member 82 pressing against and forming a seal with the skin. The sealing member may be rigid or deformable in order to provide a suitable seal. The test strip is positioned with the distal end 84 of the wicking member 83 adjacent to the incision site. The incision is formed either before or after placement of the test strip. As the bodily fluid accumulates at the incision, it contacts the wicking member and is drawn to the inlet opening 81 and into the passageway 78.

The following embodiments further demonstrate that the sampling systems are readily adapted for use with various incising, expressing and/or testing devices. Referring in particular to FIGS. 14-17, a typical lancing device is shown, except that it has been modified to include an exemplary sampling system in accordance with the present invention. The basic lancing device, absent the sampling system, is further described in U.S. Pat. No. Re 35,803, the disclosure of which is hereby incorporated by reference. Therefore, for illustrative purposes, only the major components of said device are shown in the drawings and described herein.

The lancing device 101 includes a housing 102 which contains a lancet drive mechanism 103 and a lancet holder 104. The drive mechanism includes a rotatable sleeve 105 and a spirally-wound, coiled spring 106 coupled between the housing and the rotatable sleeve. The lancet holder 104 is longitudinally slidable within the sleeve 205 and includes arms 107 with end lugs 108 that are receivable within recesses formed in a lancet component. The lancet component 109 includes a body 110 and a lancet tip 111. The lancet body defines a circumferential recess 112 which receives the end lugs 108 of the arms of the lancet holder 104. The lancet 109 is thereby longitudinally movable inside of the sleeve 105 in concert with the movement of the lancet holder 104.

The rotatable sleeve 105 includes a drive pin 113, and the lancet holder 104 defines a driver cam 114. The driver cam includes a first cam segment 115 to allow for cocking of the mechanism. The driver cam further includes a second, symmetrical, arcuate cam segment 116 to provide for projection and withdrawal of the lancet tip relative to the housing opening 117 formed in the pressing member 118 of the housing. An outer ring 119 connects with the rotatable sleeve 105 and upon rotation of the outer ring the sleeve is also rotated to tension the spring 106 as the drive pin 113 moves within the first cam segment 115. The rotatable sleeve automatically locks once in the fully tensioned position.

Upon pressing a lock release button 120, the sleeve rotates back to its original position. During this return rotation, the drive pin 113 moves within the second cam segment 116, causing the lancet holder and lancet initially to translate longitudinally of the sleeve 105 and housing 102 in a direction to drive the lancet tip to incise the skin. The lancet tip 111 is immediately thereafter withdrawn by operation of the second cam segment 116 of the lancet holder.

The pressing member extends to an annular surface 121 and defines slots 122 and 123 adjacent thereto. A test strip 124 (FIG. 16) is received within the slots 122-223 and includes an aperture 125 which is thereby positioned in line with the lancet 111. The test strip includes a sealing member 126 forming a ring surrounding the aperture 125, and further includes a capillary passageway 127 that extends from an inlet opening 128 which communicates with the aperture 125 to a test region 129. The test region includes suitable reagent to interact with the bodily fluid which is received in the test region. An optical test device 130 is mounted to the housing and is positioned to evaluate the results of the reaction in the test region.

The test strip further includes a wicking member 131 which extends into the aperture 125. The wicking member 131 is connected with the test strip at a first location adjacent to the inlet opening 128. The distal or free end of the wicking member is positioned at a second location adjacent to the incision site.

In accordance with the present invention, the integrated device 101 is operable as follows. The device is pressed against the skin 132, which thereby bears against the annular surface 121 and the sealing member 126. The lancet 111 is then advanced through the aperture 125 in the test strip and incises the skin. As a fluid droplet forms, it contacts the wicking member 131 and is drawn to the inlet opening of the capillary passageway 127, and thereafter is transported to the test region 128. The fluid then reacts with the reagent provided in the test region, and the results are read by the test device 129. The test strip may additionally include a recessed surface, as previously described, to further inhibit the passage of fluid between the skin and the underside of the test strip.

The foregoing description provides a representative sample of a lancing device useful in combination with the test strips of the present invention. It will be appreciated, however, that the particular lancing device and method are not limiting to the present invention, which finds utility with innumerable lancing systems. By way of further example, other representative lancing mechanisms include those shown in U.S. Pat. No. 4,924,879, issued to O'Brien on May 15, 1990; U.S. Pat. No. 5,879,311, issued to Duchon et al. on Mar. 9, 1999; U.S. Pat. No. 5,857,983, issued to Douglas et al. on Jan. 12, 1999; U.S. Pat. No. 6,015,392, issued to Douglas et al. on Jan. 18, 2000; U.S. Pat. No. 6,048,352, issued to Douglas et al. on Apr. 11, 2000; U.S. Pat. No. 6,183,489, issued to Douglas et al. on Feb. 6, 2001; U.S. Pat. No. 5,951,492, issued to Douglas et al. on Sep. 14, 1999; U.S. Pat. No. 5,951,493, issued to Douglas et al. on Sep. 14, 1999; U.S. Pat. No. 6,332,871, issued to Douglas et al. on Dec. 25, 2001; U.S. Pat. No. 5,964,718, issued to Duchon et al. on Oct. 12, 1999; U.S. Pat. No. 6,066,103, issued to Duchon et al. on May 23, 2000; and U.S. Pat. No. 6,086,545, issued to Roe et al. on Jul. 11, 2000.

Wicking Up a Lancet

In another aspect of the present invention, the wicking member is separate from but positioned proximate to the sampling device. The wicking member in this aspect may comprise a lancet or other incising device that is positioned adjacent to the sampling device, or another member having the primary purpose of wicking the bodily fluid to the sampling passageway.

Figure 18:
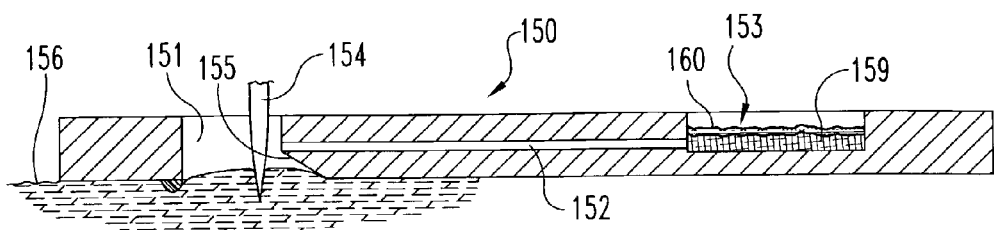
FIG. 18 is a side, cross-sectional view of a further embodiment of a test strip in accordance with the present invention, showing the placement of a lancet for drawing bodily fluid into the test strip.
Figure 19:
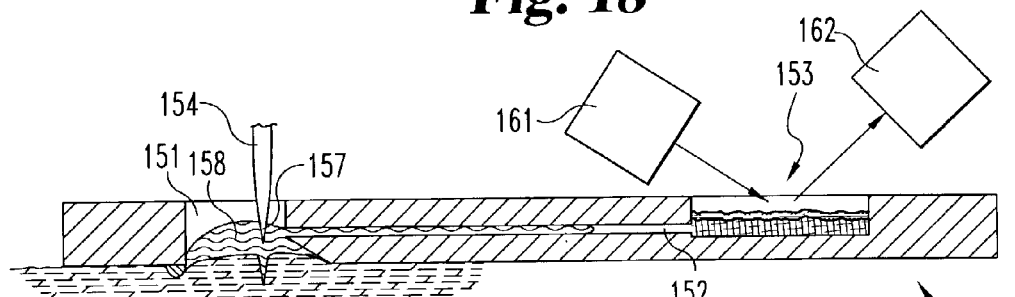
FIG. 19 is a side, cross-sectional view of the test strip of FIG. 18, showing the bodily fluid being acquired by the capillary passageway in the test strip.
Figure 20:
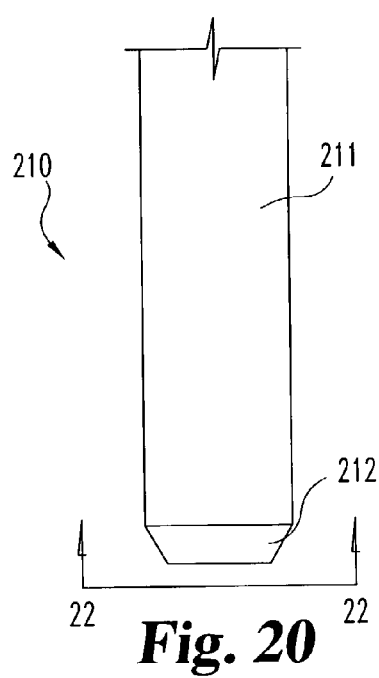
FIG. 20 is a front, elevational view of a fluid testing device including an expression system in accordance with an embodiment of the present invention.
Figure 21:
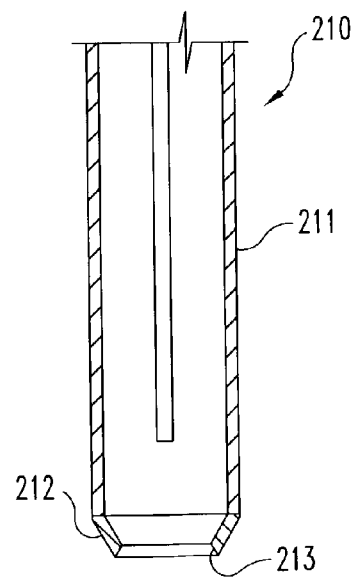
FIG. 21 is a cross-sectional view of the testing device of FIG. 20.
Figure 22:
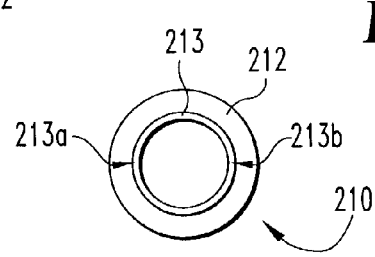
FIG. 22 is a distal end, plan view of the testing device of FIG. 20.
Figure 23:
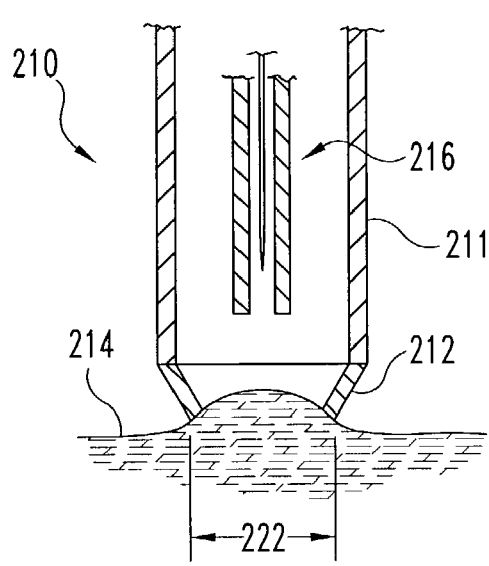
FIG. 23 is a partial, cross-sectional view of the testing device of FIG. 20.

In one respect, the invention utilizes the incising device both to form the incision and to draw the bodily fluid toward the sampling passageway. For example, shown in FIGS. 18-19 is a test strip 150 including an aperture 151, capillary passageway 152 and test area 153. However, in contrast to the embodiment of FIG. 1, the test strip 150 does not utilize a wicking member attached to the test strip. Instead, the lancet 154 is used to wick the bodily fluid to the inlet opening.

The lancet is located within the aperture 151 at the side closest to the inlet opening 155 of the sampling passageway 152. The lancet is advanced beyond the bottom surface of the test strip 150 to incise the skin 156. The lancet is then removed from the skin, but is not withdrawn from the aperture 151. Instead, the lancet is maintained with the distal tip 157 located closely adjacent to the incision site. Therefore, as bodily fluid 158 collects at the site, it will contact the distal tip 157 and will be drawn along the lancet, which is provided with a hydrophilic outer surface. As the fluid moves up along the lancet, the close proximity of the lancet to the inlet opening causes the bodily fluid to contact the inlet opening and to move into the sampling passageway. Once received within the sampling passageway, the fluid moves to the test area 153 and contacts the wicking layer 159 and the test reagent 160, and is analyzed such as by the light source 161 and reflectance meter 162.

Without the lancet being positioned in this manner, the fluid could collect in an area away from the inlet opening, such as on the left side of the aperture in FIG. 19. The presence of the lancet therefore facilitates the movement of the bodily fluid to and through the inlet opening.

An alternative embodiment of the present invention is shown in FIGS. 20-26, in which there is shown a fluid expression device 210 constructed in accordance with the present invention. Device 210 includes a housing 211 having a deformable expression member 212 at the end thereof. For purposes of illustration, the deformable member is described hereafter with respect to a flexible member. Housing 211 is typically an elongated, cylindrical member which is readily grasped by the user, but the housing may have a variety of other shapes. The material used for the housing is not critical, and may comprise, for example, various metals and plastics. The housing typically will contain other systems for incising, sampling and/or testing the bodily fluid.

Figure 24:
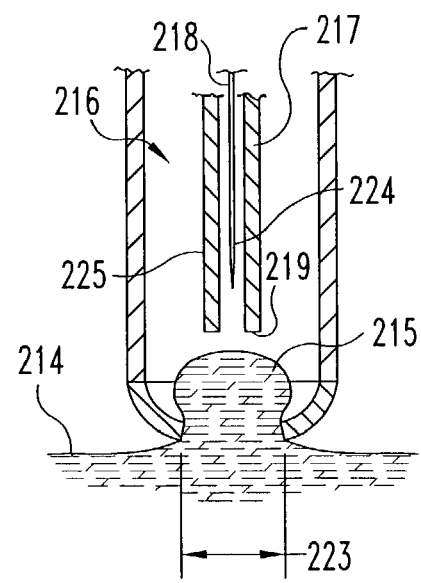
FIG. 24 is a partial cross-sectional view of the device of FIG. 20, showing the expression member in the constricting position.

The expression member 212 is connected to or integral with the housing and defines a plurality of distal end, skin-engaging surfaces, for example, 213a and 213b. In the embodiment shown, the expression member comprises a continuous, perimetric surface 213 defining the opposed, skin-engaging surfaces. The surfaces are "opposed" in the sense that movement of the surfaces will result in the constriction of the skin as previously described. The surfaces move from a first, skin-contacting position (FIG. 23) to a second, skin-constricting position (FIG. 24). The surfaces may move directly toward each other, or simply in a direction sufficient to constrict the skin.

In use, the surfaces 213 contact the skin surface 214 as the device 210 is pressed (downwardly in FIG. 23) against the skin. The device is then pressed further against the skin and the surfaces 213 engage the skin and urge the skin inward as the expression member flexes (FIG. 24). This action produces an upwardly-bulged, pinch of skin 215. The inward and upward movements of the skin-engaging surfaces constrict the skin, holding bodily fluid within the constricted area and applying a pressure that will urge the fluid toward and out of an incision.

The expression member 212 has been described as being a flexible member. This indicates that releasing the pressure and removing the device from the skin will result in a return of the member to the starting shape shown in FIG. 23. The use of a flexible member is preferable in that the device is thereby available for repeated use. However, alternatively the deformation of the member may be permanent or only partially reversible. In that event, the member will not return to its original shape.

Figure 25:
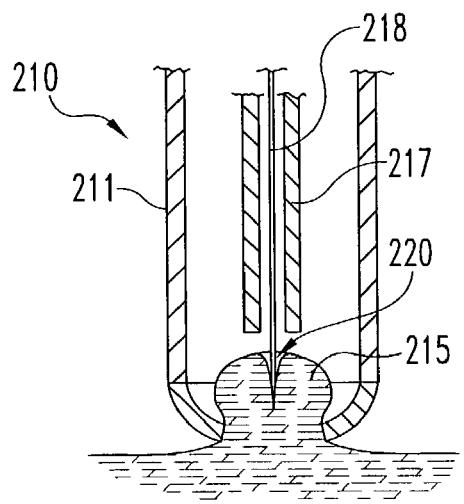
FIG. 25 is a partial cross-sectional view of the device of FIG. 20, showing the incising of the skin.

As shown in the drawings, the device 210 includes a lancing device 216 operable to incise the bulged skin. In this version, the lancing device 216 includes a capillary tube 217 and a lancet 218 longitudinally movable within the capillary tube. In accordance with the method depicted in the drawings, the lancing device 216 is positioned to have its distal end adjacent the pinch of skin formed by the constriction device (FIG. 24). The lancet 218 is then advanced beyond the end 219 of the capillary tube 217 a predetermined distance to enter the skin and form an incision 220 of desired depth (FIG. 25). The lancet 218 is then withdrawn from the incision and a drop of blood or interstitial fluid 221 exits from the incision.

The constriction of the skin adjacent the incision ensures that fluid within that region will be retained, rather than moving away from the site. The constriction of the skin further provides a bulged, pressurized pinch of skin 215 which tends to spread the incision apart after it is formed. This facilitates the expression of fluid from the incision since the skin is prevented from reclosing around the incision. In addition, the pressure maintained by the constricting member urges fluid to exit the incision once it is formed.

Figure 26:
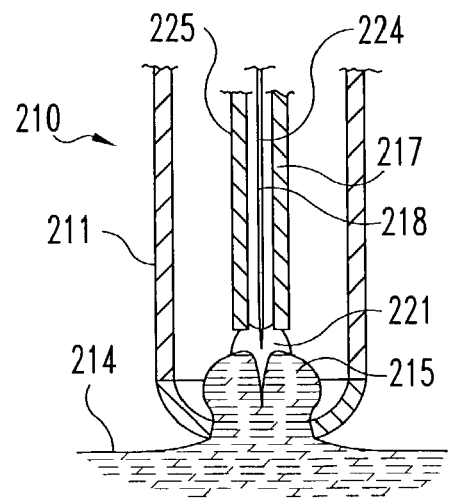
FIG. 26 is a partial cross-sectional view of the device of FIG. 20, showing the acquisition of the bodily fluid by the sampling system.

The described embodiment further demonstrates the inclusion of a sampling device useful for acquiring the fluid formed at the incision site. The capillary tube 217 defines an annular, capillary passageway 224 between the lancet 218 and the interior wall of the capillary tube. The capillary tube is positioned to be close to the fluid droplet 221 as it forms (FIG. 26). In addition, the lancet 218 is used to draw the fluid to the capillary tube in the following manner. As shown in FIG. 26, the lancet 218 is withdrawn from the incision but remains in a position extending outwardly from the capillary tube. The distal tip of the lancet is therefore positioned adjacent to the incision 220 and will be contacted by the fluid droplet 221 as it forms. The lancet is provided to be hydrophilic and will therefore draw or wick the fluid to the inlet opening of the capillary passageway 224. In the absence of the lancet being positioned as indicated, there would be the potential for the fluid to move off to the side away from the capillary tube.

The fluid is drawn upwardly into the annular passageway 224 by capillary action. This action can be enhanced by using a capillary tube having an interior passageway which is formed of a material that is naturally hydrophilic or has been treated to be hydrophilic, or which is covered, e.g., coated, with a hydrophilic material. The capillary tube may further be treated or constructed to have a hydrophobic outer surface 225 to inhibit attraction of the bodily fluid to the exterior of the capillary. Alternatively, the capillary tube may be provided with a vacuum source (not shown) in order to draw the fluid through the passageway by vacuum.

Figure 27:
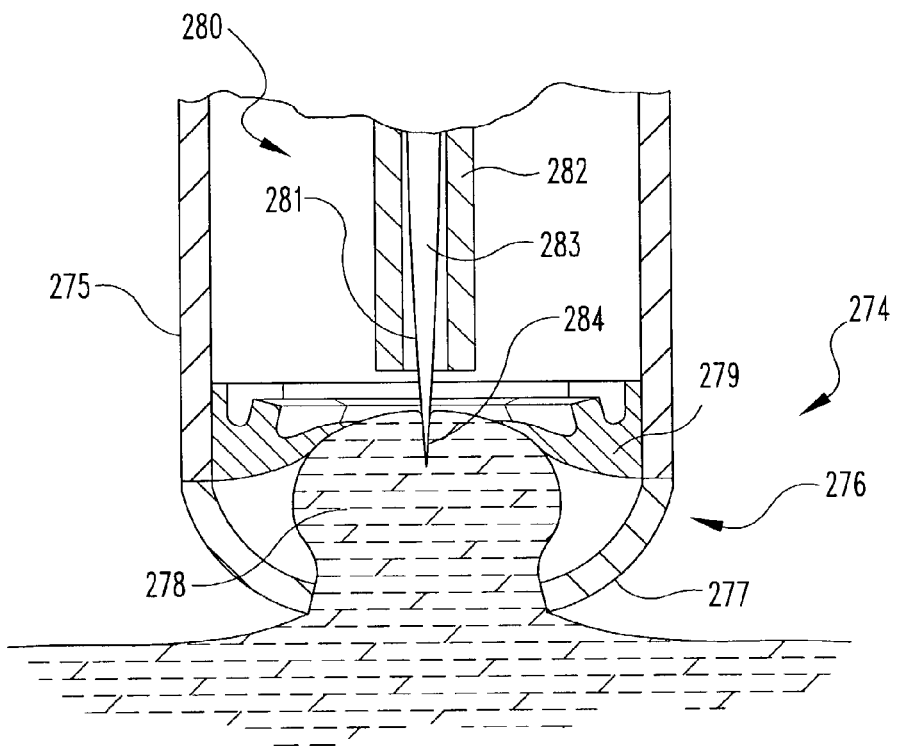
FIG. 27 is a partial, cross-sectional view of a fluid sampling device including a combined expression system in accordance with one embodiment of the present invention.
Figure 28:
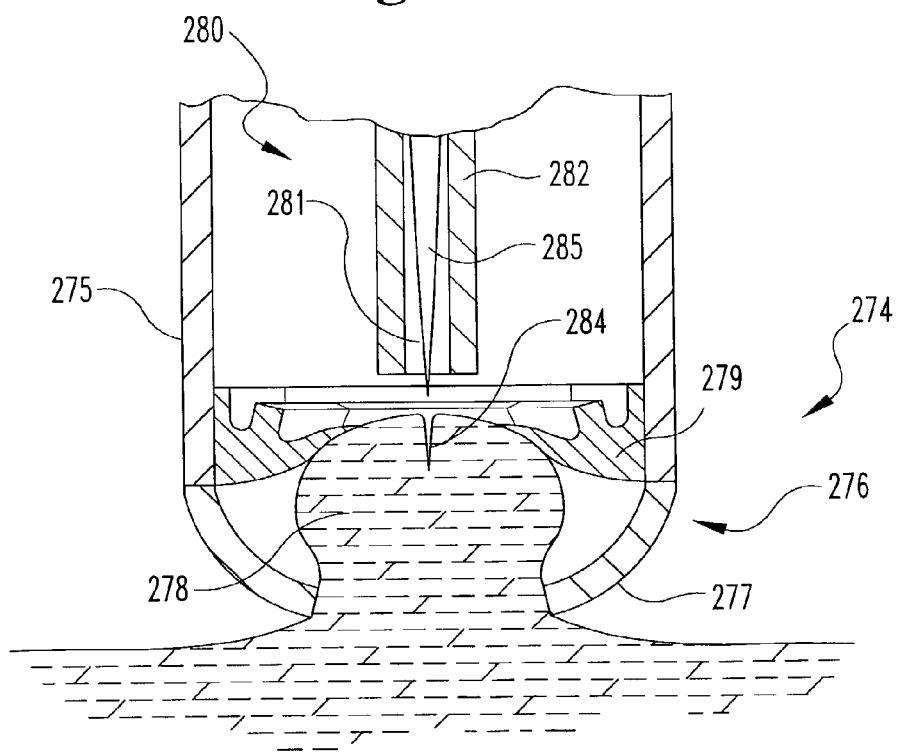
FIG. 28 is a partial, cross-sectional view of the fluid sampling device of FIG. 27 showing the acquisition of the bodily fluid.

For purposes of further illustration, there is shown in FIGS. 27-28 a testing device 274 including a housing 275 and a combination expression system 276 secured thereto. The expression system includes a constriction member 277 shown in the inner, constricting position forming the bulged pinch of skin 278. In addition, a deformable pressing member 279 is mounted in the interior of the housing 276 and is positioned to also bear on the pinch of skin 278.

As this embodiment demonstrates, the combination of the different expression systems provides a device that achieves expression in ways, and to an extent, which may not be available from the individual systems. In one sense, the combination such as shown in FIG. 27 provides the constricting function of the constriction member 276, and the pressing function of the deformable pressing member 279. In addition, it will be noted that the combination causes each system to operate somewhat differently from what might occur separately. For example, the addition of the pressing system provides additional pressure for expressing fluid, and also provides additional forces to help pull and maintain the incision open after it has formed. On the other hand, the addition of the constricting member to the deformable pressing system helps to retain fluid in the area of the skin where the pressing member is bearing against the skin. The application of a pressing member alone is accomplished by pushing the member against the skin, which may exclude fluid that is not within the perimeter of the pressing member, and further may force some fluid out of the pressing area as the device is pressed against the skin. However, in accordance with the combined system, the pressing member does not bear against the skin until the skin has already been engaged by and pulled inward by the constricting system. The skin is actually pulled up against the pressing member. Therefore, the pressing member will not exclude or force out bodily fluid in the same manner that may otherwise occur without the constricting member, and the result is that additional fluid may be available at the incision site.

The embodiment of FIGS. 27-28 also includes a capillary lancet combination 280 including a sampling passageway 281 defined between a tube 282 and a lancet 283. In contrast to the previous embodiment, the lancet 283 is fixedly attached to the tube 282 and extends outwardly therefrom, and does not move relative thereto. In use, the capillary lancet combination 280 is moved as a unit to the skin to cause the exposed distal portion of the lancet to incise the skin to the desired depth (FIG. 27). The combination unit 280 is then withdrawn from the skin to a position with the distal tip 284 of the lancet located adjacent to the incision site (FIG. 28). In this position, the lancet and tube look much like the embodiment of FIG. 26, and the acquisition of the bodily fluid occurs in the same manner.

Figure 29:
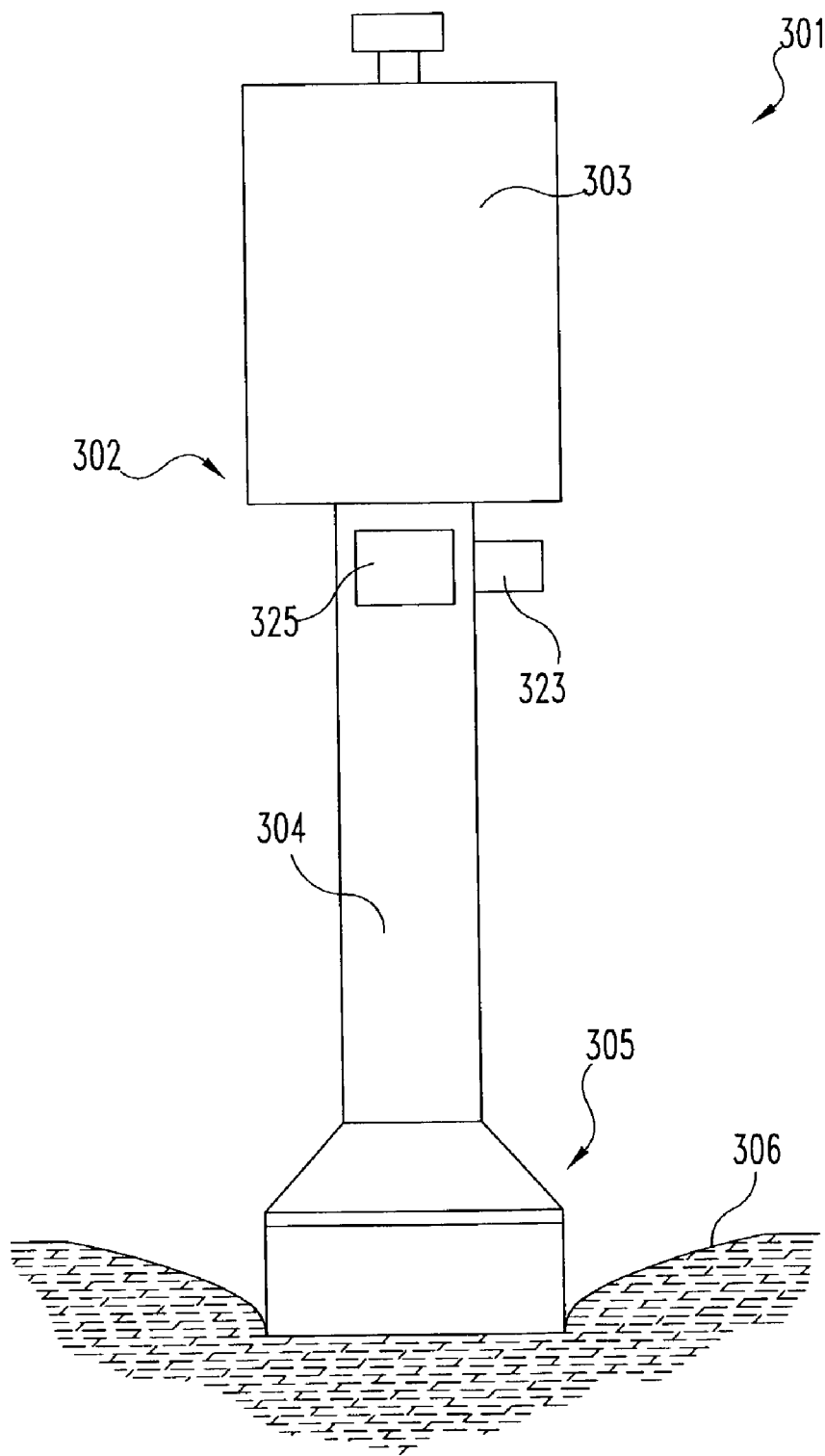
FIG. 29 is a side, elevational view of an alternate embodiment of an integrated fluid testing device according to an embodiment of the present invention.
Figure 30:
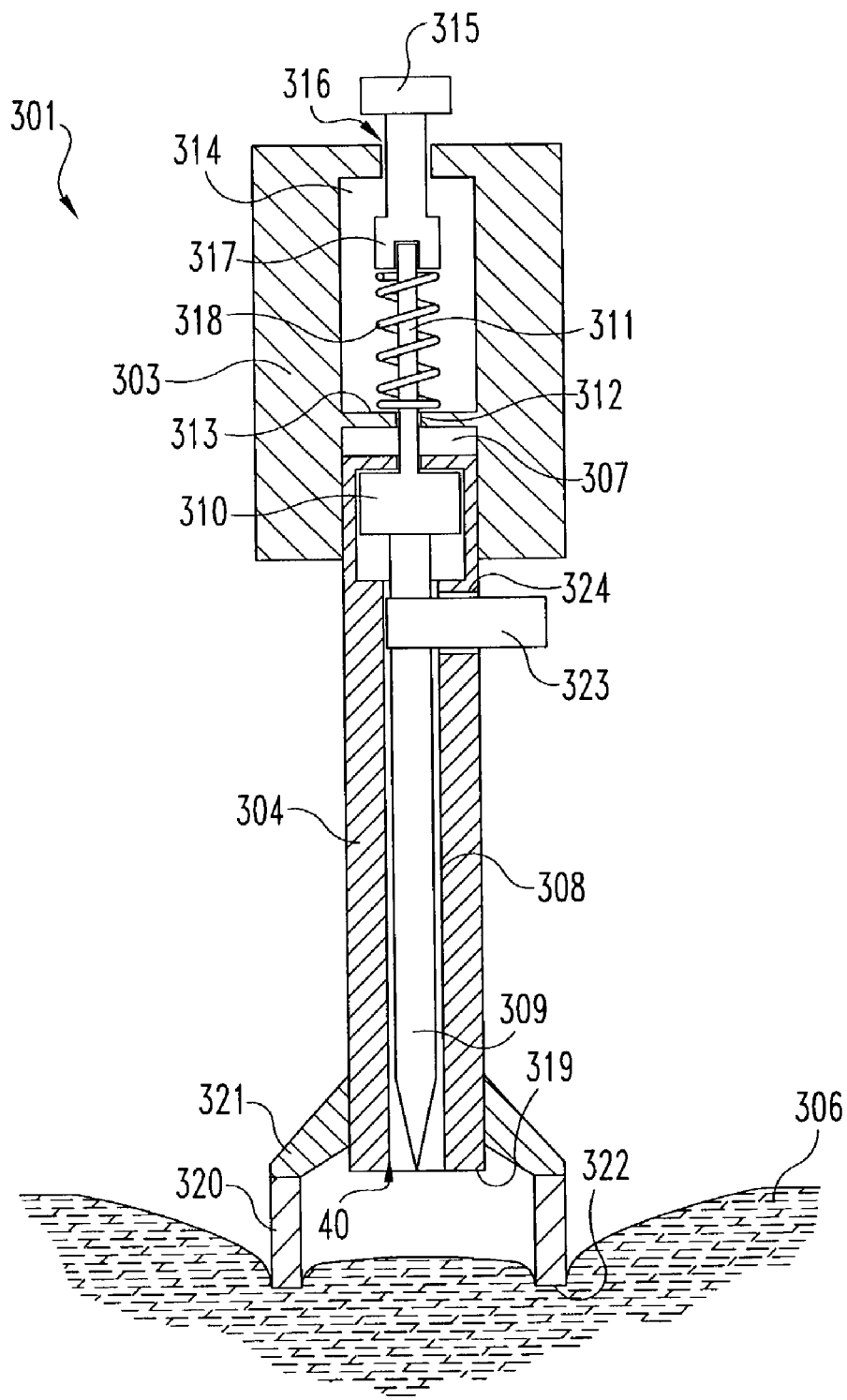
FIGS. 30 and 31 are partial, cross-sectional views of the fluid testing device of FIG. 29, showing in particular the expression of fluid from the skin and movement of the fluid up to the test area.
Figure 31:
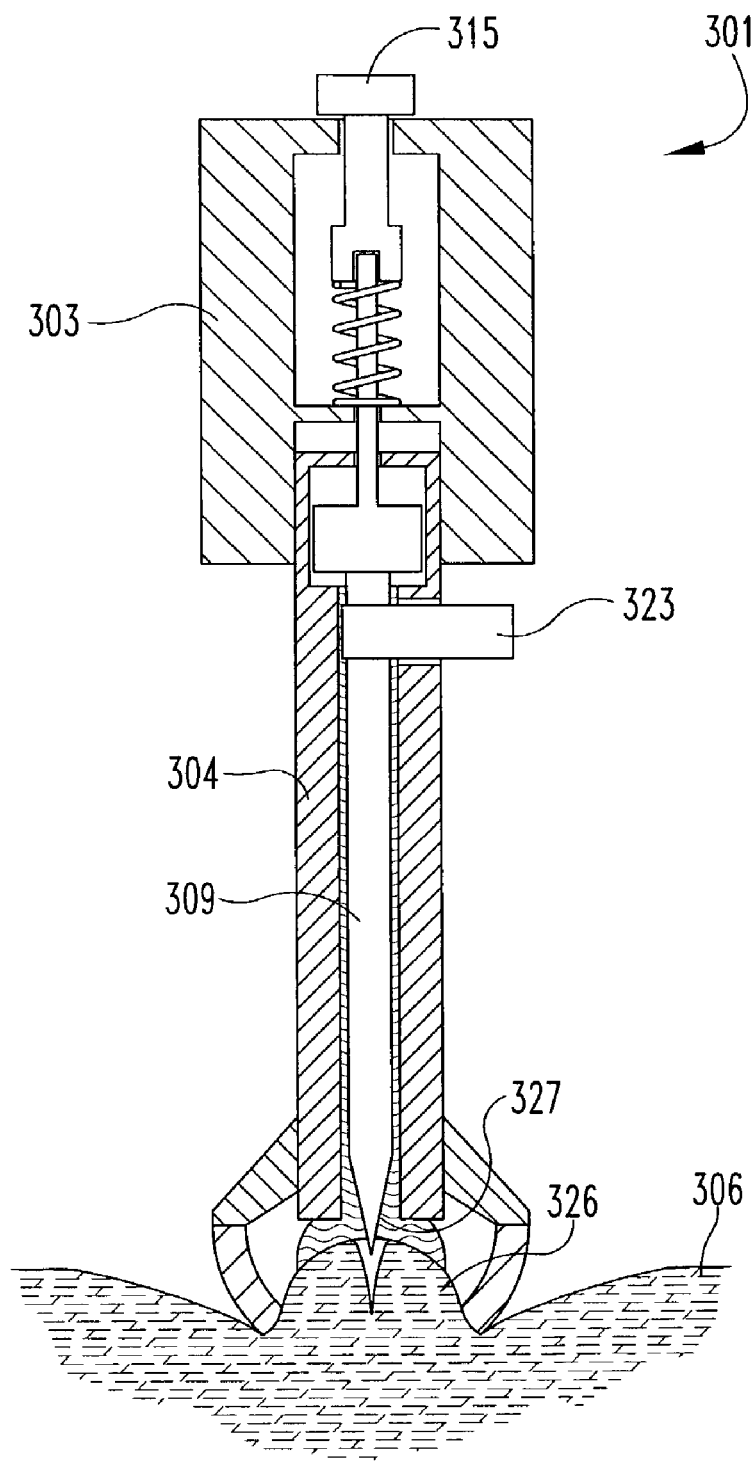

An alternate, totally integrated fluid monitoring device is shown in FIGS. 29-31. The integrated device 301 includes a housing 302 which includes or supports components operable to lance, express, sample and test bodily fluids. The housing includes a first member 303, a cylindrical extension member 304, and an expression system 305. The device 301 is shown in FIG. 29 as being contacted against the skin 306 in the position prior to expression of bodily fluid.

The components of the integrated device 301 are shown in detail beginning in FIG. 30. The cylindrical member 304 is mounted within a cavity 307 defined by the first member 303, and is secured therein, such as by a press fit or by gluing. The cylindrical member 304 defines an interior passageway 308, and a lancet 309 is received therein. The space between the lancet and the cylindrical member therefore defines an annular passageway, which is sized to provide a capillary attraction to the desired bodily fluid, as later described.

The lancet 309 is mounted to a lancet carrier 310 which includes an extension 311. The extension passes through an aperture 312 formed in an interior wall 313 of the member 302. The member 302 further defines a chamber 314 in which the extension 311 is received. A lancet button 315 is received through an aperture 316 in the member 302 and includes a mounting yoke 317 which is connected with the lancet carrier extension 311. A coil spring 318 is positioned around the extension 311 and is bears at one end on the yoke 317, and at the other end on the wall 313. In this manner, pressure applied against the button 315 will urge the lancet beyond the distal end 319 of the cylindrical member 304 for lancing the skin. Upon release of the downward pressure, the spring 318 withdraws the lancet from the incision formed in the skin to a position with the distal tip of the lancet located adjacent to the incision site (FIG. 31) the bodily fluid is again drawn into the annular capillary passageway in the manner described with respect to the previous embodiments.

The device 301 further includes an expression system 305 attached to the cylindrical member 304. In particular, the expression system includes a cylindrical expressing member 320 secured to a support 321 which is in turn attached to or formed integrally with the cylindrical member 304. The expressing member 320 is deformable to facilitate the expression of fluid from an incision positioned interior of the member. The expressing member has an initial condition in which the skin-engaging surface 322 contacts the skin at a radially-outward position (FIG. 30). Upon further pressing the device 301 against the skin, the member 320 deforms inwardly, thereby grasping and moving the skin upward and inward to a constricted position (FIG. 31). This movement applies pressure against the skin to hold bodily fluid within the constricted area and to urge the fluid toward the center.

A test strip 323 is received through an aperture 324 in the wall of the cylindrical member 304. The test strip extends within the annular passageway between the lancet 309 and the interior of the cylindrical member 304, and therefore is in position to be contacted by fluid received in the passageway. A window 325 is located in the side of the cylindrical member 304 at a position to allow the test strip to be viewed from the exterior of the device. Therefore, the results of a reaction between the bodily fluid and the test strip can be observed through the window 325. Alternative test systems, including optical and electrochemical systems for example, are equally useful in accordance with the present invention.

The integrated device is operable to provide complete lancing, expressing, sampling and testing of a bodily fluid as follows. As shown in the drawings, the device 301 is initially positioned against the skin at the locating desired for fluid acquisition. The device is then pressed against the skin sufficiently to deform the expressing member 320, as shown in FIG. 31. This results in the creation of a raised pinch of skin 326. A force is then applied to the button 315 to move the lancet downwardly into the skin to form an incision 327. The force is immediately released from the button and the lancet retracts from the incision to the position shown in FIG. 31. A droplet of bodily fluid will begin to form at the incision site, facilitated by the expressive forces applied to the skin by the expressing member 320.

As the droplet grows in size, it contacts the distal tip of the lancet 309 and is drawn to the end opening of the passageway 308. The fluid sample continues to be drawn into the passageway until it contacts the test strip 323. The test strip is selected to provide a test of the desired constituent or property of the bodily fluid being sampled. The results are obtained by optical detection of the reaction through the window 325.

Figure 32:
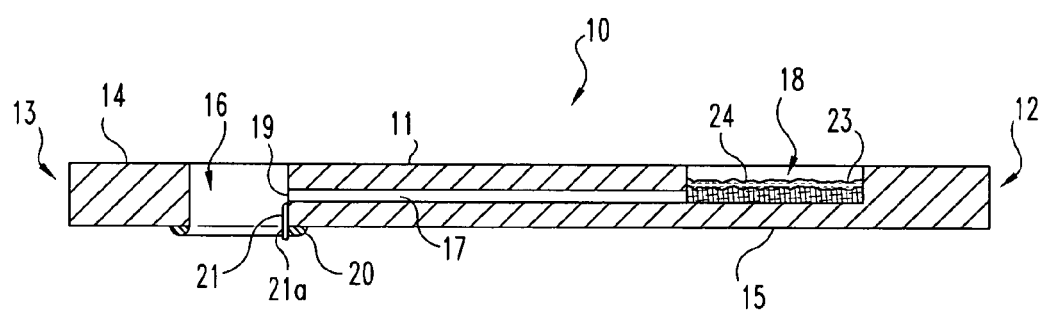
FIG. 32 is a side, cross-sectional view of a test strip according to an alternate embodiment.

In an alternate embodiment depicted in FIG. 32, the wicking member 21 has a folded section 21a that is folded against the test strip 10 or otherwise retracted from its extended position until deployed. The wicking member 21 may be deployed in various ways, such as by release of a retaining film or other member, by affirmatively moving the wicking member to the extended position, or by other means. In one approach, the operation of an incising device, e.g. a lancet, to form the incision in the skin also triggers the release of the wicking member, such as by moving a retaining film that otherwise holds the wicking member in the retracted position.

It will be appreciated from the foregoing descriptions that the several forms of wicking systems comprising the present invention are useful independently of the presence or type of incising, expressing, or testing systems. In certain embodiments, however, the sampling mechanisms and methods are combined with incising, expressing and/or testing systems. It will be appreciated by those skilled in the art that the function of the sampling system is achieved independent of these other systems, and therefore is useful with a variety of such systems as are known in the art. However, the sampling systems are advantageously combined with such other systems in a single, integrated device, and are useful in combination with a wide range of incising, expressing and testing systems, including those herein described in the description of the prior art and elsewhere, and the disclosures of such patents are hereby incorporated by reference.

As shown in the drawings, such an integrated device preferably operates such that the device does not have to be repositioned at any time during the process of incising, expressing, and/or sampling. More specifically, the device preferably carries incising, expressing, sampling and testing systems to perform a complete, integrated monitoring of the bodily fluid. In accordance with this approach, the device is moved against the skin and is maintained in this position while the incision is formed, and also while the resulting fluid droplet develops and is carried into the sampling device. The fluid is then analyzed by the test system and the result of the analysis is provided to the user. All of these actions therefore may be accomplished by a single, integrated unit, providing a simple, quick and reliable method for acquiring and testing a bodily fluid.

Closing

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A device, comprising:

an incision forming device configured to form an incision;

an analysis area configured to analyze bodily fluid from the incision;

a sampling device defining a capillary passageway that extends from the analysis area for drawing the bodily fluid via capillary action to the analysis area;

a wicking member extending from the sampling device proximal the capillary passageway to draw the bodily fluid from the incision to the sampling passageway, wherein the wicking member is an elongate member that is hydrophilic to draw the bodily fluid; and wherein the wicking member includes a folded section configured to fold against the sampling device until deployment.

2. The device of claim 1, wherein the wicking member has a uniform size and shape.

3. The sampling device of claim 1, wherein:

the sampling device has a top surface, a bottom surface and an aperture extending from the top surface to the bottom surface, the aperture being configured to surround the incision;

the capillary passageway opens into the aperture; and the wicking member extends within the aperture.

4. The sampling device of claim 3, further comprising a sealing member surrounding the aperture at the bottom surface of the sampling device to minimize fluid leakage.

5. The sampling device of claim 4, wherein the sealing member includes a hydrophobic surface to resist passage of the bodily fluid.

6. The sampling device of claim 4, further comprising a constricting system extending from the bottom surface to create a bulge of skin around the incision.

7. The sampling device of claim 3, further comprising a constricting system provided around the aperture to create a bulge of skin around the incision.

8. The sampling device of claim 7, wherein the constricting system includes at least two deformable elements positioned on opposite sides of the aperture for engaging and constricting the skin.

9. The sampling device of claim 3, wherein the sampling device has a recessed surface between the capillary passageway and the bottom surface to promote fluid flow into the capillary passageway.

10. The sampling device of claim 1, wherein the sampling device has a constricting system extending therefrom to create a bulge of skin around the incision.

11. The sampling device of claim 1, wherein the analysis area includes a test reagent covering absorbent material.

12. The sampling device of claim 1, wherein:
the sampling device has a top surface, a bottom surface and an end edge; and
the capillary passageway communicates with the end edge at a location displaced from the bottom surface.

13. The sampling device of claim 12, wherein the sampling device has a recessed surface connecting between the capillary passageway and the bottom surface.

14. The sampling device of claim 12, further comprising a sealing member located on the bottom surface to block passage of the bodily fluid.

15. The sampling device of claim 1, further comprising:
wherein the sampling device defines an aperture, the wicking member extending within the aperture; and
wherein the incision forming member includes a lancet for lancing skin, the aperture of the sampling device being positioned in alignment with the lancet in order for the lancet to lance the skin through the aperture.

* * * * *